US008744572B1

(12) United States Patent
Greenhut et al.

(10) Patent No.: US 8,744,572 B1
(45) Date of Patent: Jun. 3, 2014

(54) SYSTEMS AND METHODS FOR LEADLESS PACING AND SHOCK THERAPY

(71) Applicant: Medtronic, Inc., Minneapolis, MN (US)

(72) Inventors: Saul E. Greenhut, Aurora, CO (US); Robert J. Nehls, Lakeville, MN (US); Walter H. Olson, North Oaks, MN (US); Xusheng Zhang, Shoreview, MN (US); Wade M. Demmer, Coon Rapids, MN (US); Troy E. Jackson, New Brighton, MN (US)

(73) Assignee: Medronic, Inc., Minneapolis, MN (US)

( * ) Notice: Subject to any disclaimer, the term of this patent is extended or adjusted under 35 U.S.C. 154(b) by 0 days.

(21) Appl. No.: 13/756,085

(22) Filed: Jan. 31, 2013

(51) Int. Cl.
*A61N 1/00* (2006.01)

(52) U.S. Cl.
USPC ............................................................ 607/4

(58) Field of Classification Search
USPC ............................................................ 607/4
See application file for complete search history.

(56) References Cited

U.S. PATENT DOCUMENTS

| 5,117,824 | A | 6/1992 | Keimel et al. |
| 5,545,186 | A | 8/1996 | Olson et al. |
| 5,755,736 | A | 5/1998 | Gillberg et al. |
| 6,512,940 | B1 | 1/2003 | Brabec et al. |
| 6,522,915 | B1 | 2/2003 | Ceballos et al. |
| 6,622,046 | B2 | 9/2003 | Fraley et al. |
| 6,892,094 | B2 | 5/2005 | Ousdigian et al. |
| 7,937,135 | B2 | 5/2011 | Ghanem et al. |
| 7,991,471 | B2 | 8/2011 | Ghanem et al. |
| 7,996,087 | B2 | 8/2011 | Cowan et al. |
| 2006/0241701 | A1 | 10/2006 | Markowitz et al. |
| 2007/0088394 | A1 | 4/2007 | Jacobson |
| 2007/0088397 | A1 | 4/2007 | Jacobson |
| 2010/0228308 | A1* | 9/2010 | Cowan et al. .................... 607/14 |
| 2011/0071586 | A1* | 3/2011 | Jacobson ........................... 607/9 |
| 2011/0190835 | A1 | 8/2011 | Brockway et al. |
| 2012/0109236 | A1* | 5/2012 | Jacobson et al. .................. 607/4 |
| 2013/0066169 | A1 | 3/2013 | Rys et al. |

OTHER PUBLICATIONS

U.S. Appl. No. 13/665,492 to Bonner et al., entitled "Leadless Pacemaker System," and filed on Oct. 31, 2012.
U.S. Appl. No. 13/665,601 to Bonner et al., entitled "Leadless Pacemaker System," and filed on Oct. 31, 2012.

* cited by examiner

*Primary Examiner* — George Manuel
(74) *Attorney, Agent, or Firm* — Reed A. Duthler; Stephen W. Bauer

(57) ABSTRACT

Techniques and systems for monitoring cardiac arrhythmias and delivering electrical stimulation therapy using a subcutaneous implantable cardioverter defibrillator (SICD) and a leadless pacing device (LPD) are described. For example, the SICD may detect a tachyarrhythmia within a first electrical signal from a heart and determine, based on the tachyarrhythmia, to deliver anti-tachyarrhythmia shock therapy to the patient to treat the detected arrhythmia. The LPD may receive communication from the SICD requesting the LPD deliver anti-tachycardia pacing to the heart and determine, based on a second electrical signal from the heart sensed by the LPD, whether to deliver anti-tachycardia pacing (ATP) to the heart. In this manner, the SICD and LPD may communicate to coordinate ATP and/or cardioversion/defibrillation therapy. In another example, the LPD may be configured to deliver post-shock pacing after detecting delivery of anti-tachyarrhythmia shock therapy.

9 Claims, 14 Drawing Sheets

SYSTEMS AND METHODS FOR LEADLESS PACING AND SHOCK THERAPY

TECHNICAL FIELD

The invention relates to medical devices, and, more particularly, to implantable medical devices configured to detect and treat cardiac arrhythmias.

BACKGROUND

Implantable cardioverter defibrillators may be used to deliver high energy cardioversion or defibrillation shocks to a patient's heart when atrial or ventricular fibrillation is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by the ICD.

Currently, ICDs use endocardial or epicardial leads which extend from the ICD housing through the venous system to the heart. Electrodes positioned in or adjacent to the heart by the leads are used for pacing and sensing functions. Cardioversion and defibrillation shocks (e.g., anti-tachyarrhythmia shocks) are generally applied between a coil electrode carried by one of the leads and the ICD housing, which acts as an active can electrode.

In addition, or as an alternative to cardioversion and defibrillation shocks, the ICD or an implantable artificial pacemaker may provide cardiac pacing therapy to the heart when the natural pacemaker and/or conduction system of the heart fails to provide synchronized atrial and ventricular contractions at rates and intervals sufficient to sustain healthy patient function. Such antibradycardial pacing may provide relief from symptoms, or even life support, for a patient. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by conventional pacemakers and/or ICDs is usually provided by a pulse generator implanted subcutaneously or sub-muscularly in or near a pectoral region of a patient. The generator typically connects to the proximal end of one or more implanted leads, the distal end of which contains one or more electrodes for positioning adjacent to the inside or outside wall of a cardiac chamber. Each of the leads may be secured near or against the cardiac tissue to provide sufficient transmission of electrical energy to the cardiac tissue in order to capture the heart.

SUMMARY

Generally, this disclosure describes various techniques and systems for monitoring tachyarrhythmias and delivering anti-tachycardia therapy using a subcutaneous implantable cardioverter defibrillator (SICD) and/or an anti-tachycardia pacing device (ATPD) such as a leadless pacing device (LPD). The SICD may be implanted external to a rib cage of a patient without any leads implanted within the rib cage or within the vasculature. The SICD may also be configured to detect tachyarrhythmias and/or deliver anti-tachyarrhythmia shock therapy (e.g., cardioversion shocks or defibrillation shocks). The LPD may be implanted within a chamber of the heart and include one or more electrodes for monitoring cardiac signals and/or delivering anti-tachycardia pacing therapy, for example.

In addition, the SICD and the LDP may be configured to engage in one-way or two-way communication between the SICD and the LPD. This one-way or two-way communication may be used to initiate therapy and/or confirm that therapy should be delivered. For example, one-way communication may allow the SICD to detect a tachyarrhythmia and transmit a communication message to the LPD instructing the LPD to deliver anti-tachycardia pacing (ATP) prior to the SICD delivering an anti-tachyarrhythmia shock.

As another example, two-way communication may allow confirmation of a detected tachyarrhythmia prior to delivery of any therapy. For example, the SICD may request a communication message from the LPD confirming a detected tachyarrhythmia prior to delivering an anti-tachyarrhythmia shock or the LPD may request a communication message from the SICD confirming the tachyarrhythmia prior to delivering ATP. Since the sensing vectors of the SICD electrodes outside of the patient's rib cage may be different than the sensing vectors of the LPD electrodes within the heart, confirming tachyarrhythmias using different vectors from the SICD and the LPD may reduce false positives. In some examples, the LPD may also be configured to deliver post-shock pacing to the heart of the patient.

In one example, the disclosure describes a method that includes sensing a first electrical signal from a heart of a patient, detecting a tachyarrhythmia within the sensed first electrical signal, determining, by a subcutaneous implantable cardioverter defibrillator (SICD) and based on the detected tachyarrhythmia, to deliver anti-tachyarrhythmia shock therapy to the patient to treat the detected arrhythmia, and receiving, by a leadless pacing device (LPD) implanted within the heart of the patient, communication from the SICD requesting the LPD deliver anti-tachycardia pacing to the heart. The method also includes sensing, by the LPD, a second electrical signal from the heart of the patient and determining, by the LPD and based on the second electrical signal, whether to deliver anti-tachycardia pacing to the heart from the LPD.

In another example, the disclosure describes a system that includes a subcutaneous implantable cardioverter defibrillator (SICD) comprising a first set of electrodes and configured to sense a first electrical signal from a heart of a patient via the one or more first electrodes, detect a tachyarrhythmia within the sensed first electrical signal, and determine, based on the detected tachyarrhythmia, to deliver anti-tachyarrhythmia shock therapy to the patient to treat the detected arrhythmia. The system also includes a leadless pacing device (LPD) comprising a second set of electrodes and configured to be implanted within the heart of the patient, wherein the LPD is configured to receive communication from the SICD requesting the LPD deliver anti-tachycardia pacing to the heart, sense a second electrical signal from the heart of the patient via the second set of electrodes, and determine, based on the second electrical signal, whether to deliver anti-tachycardia pacing to the heart.

In another example, the disclosure describes a subcutaneous implantable cardioverter defibrillator (SICD), the SICD including a housing configured to be implanted in a patient external to a rib cage of the patient, one or more electrodes configured to be disposed external to the rib cage, a shock module configured to at least partially deliver anti-tachyarrhythmia shock therapy to a patient via the one or more electrodes, a communication module configured to at least one of transmit or receive communication messages between a leadless pacing device (LPD) configured to be implanted within a heart of the patient, and a sensing module configured to sense an electrical signal from the heart of the patient via the one or more electrodes. The SICD also includes a processor configured to detect a tachyarrhythmia within the sensed electrical signal, determine, based on the detected tachyarrhythmia, to deliver anti-tachyarrhythmia shock therapy to the patient to treat the detected tachyarrhythmia, and transmit, via the communication module and prior to delivering anti-tachyarrhythmia shock therapy, a communication message to the LPD requesting the LPD deliver anti-tachycardia pacing to the heart of the patient.

In another example, the disclosure describes a leadless pacing device (LPD), the LPD including a housing configured to be implanted within a heart of a patient, one or more electrodes coupled to the housing, a fixation mechanism configured to attach the housing to tissue of the heart, a sensing module configured to sense an electrical signal from the heart of the patient via the one or more electrodes, and a signal generator configured to deliver anti-tachycardia pacing therapy to the heart of the patient via the one or more electrodes. The LPD also includes a processor configured to receive a communication message from a subcutaneous implantable cardioverter defibrillator (SICD) requesting the LPD deliver anti-tachycardia pacing to the heart, wherein the SICD is configured to be implanted exterior to a rib cage of the patient, determine, based on the sensed electrical signal, whether to deliver anti-tachycardia pacing to the heart, and in response to the determination, command the signal generator to deliver the anti-tachycardia pacing therapy.

In another example, the disclosure describes a method that includes sensing a first electrical signal from a heart of a patient, detecting a tachyarrhythmia within the sensed first electrical signal, determining, by a subcutaneous implantable cardioverter defibrillator (SICD) and based on the detected tachyarrhythmia, to deliver anti-tachyarrhythmia shock therapy to the patient to treat the detected tachyarrhythmia, transmitting, by the SICD, communication requesting that a leadless pacing device (LPD) deliver anti-tachycardia pacing to the heart, receiving, by the LPD, the communication from the SICD requesting that the LPD deliver anti-tachycardia pacing to the heart, and, in response to receiving the communication, delivering, via one or more electrodes of the LPD, anti-tachycardia pacing to the heart of the patient.

In another example, the disclosure describes a method that includes receiving, by a leadless pacing device (LPD), an indication of a detected cardiac arrhythmia eligible for anti-tachyarrhythmia shock therapy, wherein the LPD comprises a set of electrodes and is configured to be implanted within a heart of a patient and, in response to receiving the indication, enabling, by the LPD, a shock detector configured to detect delivery of anti-tachyarrhythmia shock therapy, wherein the LPD comprises the shock detector. The method also includes detecting, by the shock detector, delivery of anti-tachyarrhythmia shock therapy and, in response to the detection, delivering, by the LPD and via at least a subset of the set of electrodes, post-shock pacing therapy to the heart of the patient.

The details of one or more examples are set forth in the accompanying drawings and the description below. Other features, objects, and advantages will be apparent from the description and drawings, and from the claims.

DETAILED DESCRIPTION

Figure 1:
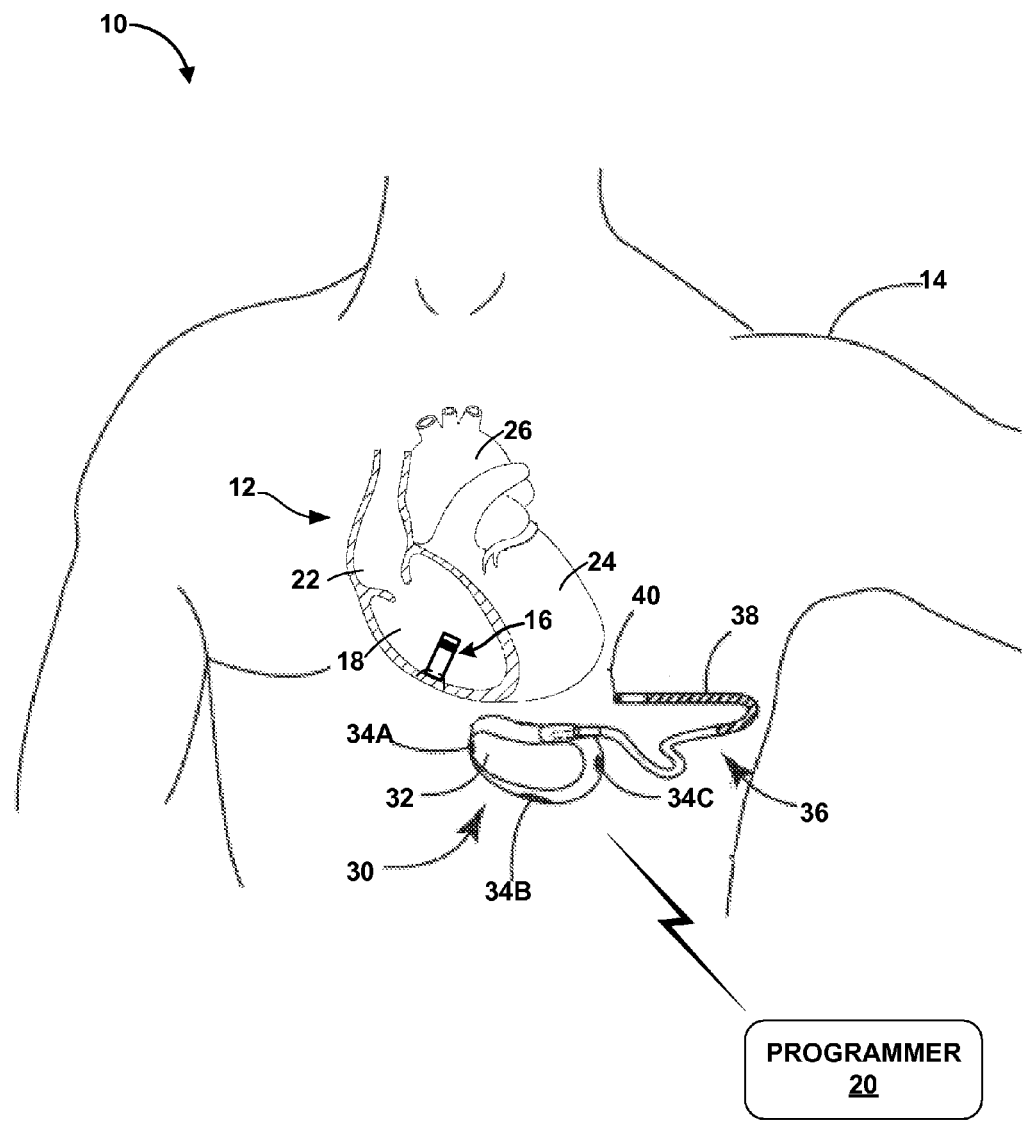
FIG. 1 is a conceptual drawing illustrating an example system that includes a subcutaneous implantable cardioverter defibrillator (SICD) implanted exterior to the rib cage of a patient and a leadless pacing device (LPD) implanted within a cardiac chamber of the patient.

This disclosure describes various techniques and systems for monitoring tachyarrhythmias and delivering anti-tachycardia therapy using a subcutaneous implantable cardioverter defibrillator (SICD) and a leadless pacing device (LPD). Typically, an SICD may be configured to detect tachyarrhythmias and deliver anti-tachyarrhythmia shock therapy from one or more electrodes implanted subcutaneously, such as external to the ribcage of the patient. The SICD may thus deliver shocks to the patient without any leads implanted within the vasculature and/or heart of the patient. However, the absence of endocardial or epicardial electrodes may decrease cardiac signal sensitivity and/or make sensing arrhythmias more challenging. For example, muscle movement, respiration, posture variations, and other physiological signal sources and environmental noises may affect the ability of the SICD to detect arrhythmias from sensed electrocardiogram (ECG) signals. Moreover, the absence of endocardial or epicardial electrodes decreases the ability of the SICD to provide pacing therapy to the patient.

One or more LPDs carrying one or more electrodes may be implanted within various chambers of the heart of the patient or otherwise in close proximity of the cardiac muscle. At these locations, an LPD may sense ECG signals with high signal-to-noise ratios to detect arrhythmias. In addition, an LPD may provide cardiac pacing at the location of the implanted LPD. However, one or more LPDs may not be capable of delivering an anti-tachyarrhythmia shock or sensing far-field ECG signals indicative of global cardiac condition.

Therefore, this disclosure describes techniques for monitoring the patient and/or delivering therapy to the patient via an SICD and one or more LPDs. For example, the SICD may communicate with an LPD using one-way or two-way communication. This communication may enable a system level of functionality such as sharing the detection of arrhythmias between devices, synchronized timing of anti-tachyarrhythmia shocks, anti-tachycardia pacing (ATP), and/or post-shock pacing, and optimization of the resources (e.g., battery capacity or processing power) available to each device. In some examples, one or both of SICD and LPD may share detected signals or physiological information (e.g., R-R intervals, electrogram morphology measurements, and/or electrocardiograms or electrograms) such that the device receiving such information can determine a condition of patient 14 (e.g., determine whether or not patient 14 is experiencing an arrhythmia).

In some examples, communication between the SICD and an LPD may be used to initiate therapy and/or confirm that therapy should be delivered. For example, one-way communication may allow the SICD to detect a tachyarrhythmia and transmit a communication message to the LPD instructing the LPD to deliver ATP prior to the SICD delivering an anti-tachyarrhythmia shock. The SICD may also identify ineffective ATP and transmit a communication message to the LPD instructing the LPD to change one or more parameters that define the ATP therapy. In this one-way communication example the SICD may be configured to transmit communications to the LPD and the LPD may be configured to receive the communication from the SICD. Alternatively, one-way communication may be established such that the LPD may be configured to transmit communications to the SICD (e.g., communication indicating that LPD 16 is detecting a tachyarrhythmia).

In other examples, two-way communication may allow confirmation of a detected tachyarrhythmia prior to delivery of any therapy. For example, the SICD may first detect a tachyarrhythmia eligible for an anti-tachyarrhythmia shock. In response to the detection, the SICD may transmit a communication message to the LPD requesting a reply from the LPD confirming a detected tachyarrhythmia prior to delivering an anti-tachyarrhythmia shock. In addition to the confirmation request received from the SICD, the LPD may receive instructions to deliver ATP while the SICD is preparing to deliver a shock (e.g., charging a shock module). The LPD may transmit confirmation that ATP is being delivered or any other status message concerning detected arrhythmias and/or delivered therapies. In alternative examples, SICD may wait for LPD to deliver one or more sessions of ATP before beginning to charge the shock module. In this manner, the SICD may not need to charge the shock module in situations in which ATP is effective at terminating the tachyarrhythmia. SICD may determine if charging the shock module occurs during ATP delivery of after confirmation that ATP was unsuccessful.

In another example, the LPD may first detect a tachyarrhythmia eligible for an anti-tachyarrhythmia shock and/or ATP therapy. The LPD may transmit a communication message to the SICD requesting confirmation of the tachyarrhythmia. In response to detecting the tachyarrhythmia, the SICD may then transmit a confirmation message to the LPD. The SICD may then begin charging for delivery of an anti-tachyarrhythmia shock and the LPD may deliver ATP prior to delivery of the shock. In some examples, the SICD may transmit a communication message informing the LPD that ATP is not effective (e.g., capturing the cardiac rhythm) and/or that a shock will be delivered and/or has been delivered.

In other examples, the LPD may also be configured to deliver post-shock pacing to the heart of the patient. In response to detecting an arrhythmia eligible for anti-tachyarrhythmia shock therapy and/or receiving a communication from an SICD that a shock will be delivered, the LPD may enable a shock detector or otherwise place itself into a shock ready state for a predetermined period of time. In response to detection of a shock delivered to the patient or after a predetermined period of time has elapsed, the LPD may deliver post-shock pacing therapy to the heart of the patient. The LPD may restart post-shock pacing in response to detecting another shock and/or continue post-shock pacing until a timeout threshold is reached.

In these and other examples, an SICD may be configured to communicate with one or more LPDs implanted within the same patient. The SICD and LPDs may utilize different communication protocols. For example, communication messages may be transmitted using radio-frequency telemetry, inductive coupling, electrical signals from implanted electrodes, or any other mechanism.

Although the monitoring and therapy techniques described herein are generally described with respect to a single SICD and a single LPD, multiple SICDs and/or LPDs may be used in conjunction with each other. For example, a single SICD may communicate with one or more of LPDs implanted within respective atria and/or ventricles of the heart. In this example, multiple LPDs may monitor respective chamber activity and/or deliver location specific pacing therapy. In some examples, the LPDs may be configured to coordinate pacing signals between each chamber.

FIG. 1 is a conceptual drawing illustrating an example system 10 that includes a subcutaneous implantable cardioverter defibrillator (SICD) 30 implanted exterior to a rib cage of patient 14 and a leadless pacing device (LPD) 16 implanted within right ventricle 18 of patient 14. In the example of FIG. 1, system 10 includes LPD 16 and SICD 30. External programmer 20 may be configured to communicate with one or both of LPD 16 and SICD 30. Generally, there are no wires or other direct electrical (e.g., hardwired) connections between SICD 30 and LPD 16. In this manner, any communication between SICD 30 and LPD 16 may be described as "wireless" communication. Patient 14 is ordinarily, but not necessarily, a human patient.

SICD 30 includes a housing 32 configured to be subcutaneously implanted outside the rib cage of patient 14. The subcutaneous implantation location may be anterior to the cardiac notch, for example. In addition, housing 32 may carry three subcutaneous electrodes 34A-34C (collectively "electrodes 34"). In other examples, housing 32 may carry fewer or greater than three electrodes. Lead 36 may be configured to couple to housing 32 and extend from housing 32 to a different subcutaneous location within patient 14. For example, lead 36 may be tunneled laterally and posteriorly to the back of patient 14 at a location adjacent to a portion of a latissimus dorsi muscle. Lead 36 may carry electrode coil 38 along a length of lead 36 and sensing electrode 40 at a distal end of lead 36. SICD 30 may be configured such that heart 12 may be disposed at least partially between housing 30 and electrode coil 38 of lead 36. In some examples, lead 36 may carry two or more electrode coils 38 and/or two or more sensing electrodes 40.

SICD 30 may contain, within housing 32, signal processing and therapy delivery circuitry to detect arrhythmias (e.g., bradycardia and tachycardia conditions) and to apply appropriate pacing and/or anti-tachyarrhythmia shock therapy (e.g., defibrillation or cardioversion shocking pulses) to heart 12. SICD 30 may be configured to apply pacing pulses via one or more electrodes 34. SICD 30 may be configured to apply the anti-tachyarrhythmia shock pulses between coil electrode 38 and one or more of electrodes 34 and/or the electrically conductive housing 32 (e.g., an additional can electrode) of SICD 30. SICD 30 may be configured to communicate with programmer 20 via an RF communication link, inductive coupling, or some other wireless communication protocol.

SICD 30 differs from traditionally used ICDs in that housing 32 may be larger in size than the housing of a traditional ICD to accommodate larger capacity batteries, for example. In addition, SICD 30 may be implanted subcutaneously whereas a traditional ICD may be implanted under muscle or deeper within patient 14. In other examples, housing 32 may be shaped or sized differently to be implanted subcutaneously instead of under a muscle or within deep tissue. Moreover, SICD 30 does not include leads configured to be placed in the bloodstream (e.g., endocardial or epicardial leads). Instead, SICD 30 may be configured to carry one or more electrodes (e.g., electrodes 34) on housing 32 together with one or more subcutaneous leads (e.g., lead 36) that carry defibrillation coil electrode 38 and sensing electrode 40. In other examples, lead 36 may include additional electrodes. These subcutaneously implanted electrodes of SICD 30 may be used to provide therapies similar to that of traditional ICDs without invasive vascular leads. In other examples, the exact configuration, shape, and size of SICD 30 may be varied for different applications or patients. Although SICD 30 is generally described as including one or more electrodes, SICD 30 may typically include at least two electrodes to deliver an electrical signal (e.g., therapy) and/or provide at least one sensing vector.

System 10 also includes one or more LDPs, such as LPD 16. LPD 16 may be, for example, an implantable leadless pacing device (e.g., a pacemaker, cardioverter, and/or defibrillator) that provides electrical signals to heart 12 via electrodes carried on the housing of LPD 16. In the example of FIG. 1, LPD 16 is implanted within right ventricle 18 of heart 12 to sense electrical activity of heart 12 and/or deliver electrical stimulation, e.g., anti-tachycardia pacing (ATP), to heart 12. LPD 16 may be attached to a wall of the right ventricle 18 via one or more fixation elements that penetrate the tissue. These fixation elements may secure LPD 16 to the cardiac tissue and retain an electrode (e.g., a cathode or an anode) in contact with the cardiac tissue. LPD 16 may also include one or more motion sensors (e.g., accelerometers) configured to detect and/or confirm tachyarrhythmias from these mechanical motions of heart 12. Since LPD 16 includes two or more electrodes carried on the exterior housing of LPD 16, no other leads or structures need to reside in other chambers of heart 12. However, in other examples, system 10 may include additional LPDs within respective chambers of heart 12 (e.g., right atrium 22 and/or left ventricle 24).

In other examples, LPD 16 may be implanted within right atrium 22, left ventricle 24, or the left atrium 26. LPD 16 may be attached to a location of heart 12 that is appropriate for propagation of electrical stimulus delivered by LPD 16. For example, LPD 16 may be implanted at a site appropriate to provide ATP therapy to heart 12 during a detected tachyarrhythmia and prior to delivery of an anti-tachyarrhythmia shock. However, LPD 16 may be positioned in a variety of locations within heart 12. In some examples, LPD 16 may be implanted via an intravenous catheter that is inserted through one or more veins and into the desired right atrium 22 or right ventricle 18. In other examples, LPD 16 may be attached to an external surface of heart 12 (e.g., in contact with the epicardium) such that LPD 16 is disposed outside of heart 12. For attachment to the external surface of heart 12, a clinician may need to perform an arthroscopic or other minimally invasive surgical technique to implant LPD 16, for example.

Using the electrodes carried on the housing of LPD 16, LPD 16 may be capable sensing intrinsic electrical signals, e.g., an electrocardiogram (ECG). SICD 30 may similarly sense intrinsic electrical signals from the sensing vectors of electrodes 34, 38, and 40. These intrinsic signals may be electrical signals generated by cardiac muscle and indicative of depolarizations and repolarizations of heart 12 at various times during the cardiac cycle. LPD 16 may generate an electrogram from these cardiac signals that may be used by LPD 16 to detect arrhythmias, such as tachyarrhythmias, or identify other cardiac events, e.g., ventricle depolarizations or atrium depolarizations. LPD 16 may also measure impedances of the carried electrodes and/or determine capture thresholds of those electrodes intended to be in contact with cardiac tissue. In addition, LPD 16 may be configured to communicate with external programmer 20.

The configurations of electrodes used by LPD 16 for sensing and pacing may be typically considered bipolar. However, unipolar ATPDs may be provided with a lead to an additional electrode. LPD 16 may detect arrhythmia of heart 12, such as tachycardia or fibrillation of the right atrium 22, left atrium 26 and/or ventricles 18 and 24, and may also provide pacing therapy via the electrodes carried by the housing of LPD 16. Although LPD 16 is generally described as providing pacing therapy and SICD 30 is generally described as providing anti-tachyarrhythmia shock therapy, in some examples, LPD 16 may be configured to provide anti-tachyarrhythmia shock therapy and SICD 30 may be configured to provide pacing therapy.

External programmer 20 may be configured to communicate with one or both of SICD 30 and LPD 16. In examples where external programmer 20 only communicates with one of SICD 30 and LPD 16, the non-communicative device may receive instructions from or transmit data to the device in communication with programmer 20. In some examples, programmer 20 comprises a handheld computing device, computer workstation, or networked computing device. Programmer 20 may include a user interface that receives input from a user. In other examples, the user may also interact with programmer 20 remotely via a networked computing device. The user may interact with programmer 20 to communicate with LPD 16 and/or SICD 30. For example, the user may interact with programmer 20 to send an interrogation request and retrieve therapy delivery data, update therapy parameters that define therapy, manage communication between LPD 16 and/or SICD 30, or perform any other activities with respect to LPD 16 and/or SICD 30. Although the user is a physician, technician, surgeon, electrophysiologist, or other healthcare professional, the user may be patient 14 in some examples.

Programmer 20 may also allow the user to define how LPD 16 and/or SICD 30 senses electrical signals (e.g., ECGs), detects arrhythmias such as tachyarrhythmias, delivers therapy, and communicates with other devices of system 10. For example, programmer 20 may be used to change tachyarrhythmia detection parameters. In another example, programmer 20 may be used to manage therapy parameters that define therapies such as anti-tachyarrhythmia shocks and/or ATP. Moreover, programmer 20 may be used to alter communication protocols between LPD 16 and SICD 30. For example, programmer 20 may instruct LPD 16 and/or SICD 30 to switch between one-way and two-way communication and/or change which of LPD 16 and/or SICD 30 are tasked with initial detection of arrhythmias.

Programmer 20 may communication with LPD 16 and/or SICD 30 via wireless communication using any techniques known in the art. Examples of communication techniques may include, for example, radiofrequency (RF) telemetry, but other techniques are also contemplated. In some examples, programmer 20 may include a programming head that may be placed proximate to the patient's body near the LPD 16 and/or SICD 30 implant site in order to improve the quality or security of communication between LPD 16 and/or SICD 30 and programmer 20.

As described herein, LPD 16 and SICD 30 may engage in communication to facilitate the appropriate detection of arrhythmias and/or delivery of anti-tachycardia therapy. As described herein, anti-tachycardia therapy may include anti-tachyarrhythmia shocks (e.g., cardioversion or defibrillation shocks) and/or anti-tachycardia pacing (ATP). The communication may include one-way communication in which one device is configured to transmit communication messages and the other device is configured to receive those messages. The communication may instead include two-way communication in which each device is configured to transmit and receive communication messages. Although the examples below describe detection of tachyarrhythmias and the delivery of anti-tachyarrhythmia shocks and/or ATP, LPD 16 and SICD 30 may be configured to communicate with each other provide alternative electrical stimulation therapies.

In one example process, system 10 may sense a first electrical signal from heart 12 of patient 14, detect a tachyarrhythmia within the sensed first electrical signal, and determine, by SICD 30 and based on the detected arrhythmia, to deliver anti-tachyarrhythmia shock therapy to patient 14 to treat the detected arrhythmia. The process may also include receiving, by LPD 16 implanted within heart 12 of patient 14, communication from SICD 30 requesting LPD 16 deliver anti-tachycardia pacing to heart 12 and sensing, by LPD 16, a second electrical signal from heart 12. LPD 16 may also be configured to determine, based on the second electrical signal, whether to deliver ATP to heart 12 from LPD 16.

LPD 16 may thus determine to deliver ATP to heart 12 and deliver, via one or more electrodes of LPD 16, ATP to heart 12 of patient 14. In some examples, LPD 16 may be configured to determine, based on a sensed electrical signal, one or more parameter values that at least partially determine the ATP. For example, LPD 16 may use an algorithm to identify one or more of the pulse rate, pulse width, pulse amplitude (e.g., voltage or current), electrode configuration, electrode polarity, or any other therapy parameter values. One or more of these values may be based on one or more aspects of the detected arrhythmia (e.g., frequency, variation, etc.). In response to determining the one or more parameter values, LPD 16 may proceed to deliver the ATP therapy. In some examples, such as two-way communication, LPD 16 may also be configured to transmit a communication message to SICD 30 confirming the determination to deliver ATP, the determined ATP parameter values, and/or completion of ATP delivery.

LPD 16 may also be configured to determine, based on the sensed electrical signal from heart 12, not to deliver ATP. This determination may be made when LPD 16 does not detect any tachyarrhythmias within the sensed electrical signal. Alternatively, the determination not to deliver ATP may be made based on a low battery level, detected electrode or delivery circuit malfunction, or any other issue even when a tachyarrhythmia has been detected by LPD 16. In response to the determination not to deliver anti-tachycardia pacing, LPD 16 may transmit, to SICD 30, communication identifying the determination that was made not to deliver ATP.

In some examples, SICD 30 may proceed with the delivery of a shock when ATP has not been delivered. In other examples, SICD 30 may terminate charging or cease delivery of a shock if LPD 16 does not deliver ATP. SICD 30 may thus interpret the determination not to deliver ATP as meaning LPD 16 did not confirm the SICD detection of a tachyarrhythmia. In this manner, SICD 30 may be configured to receive the communication from LPD 16 identifying the determination not to deliver ATP and overturn, based on the received communication identifying the determination not to deliver ATP, the determination to deliver anti-tachyarrhythmia shock therapy to patient 14. In other examples, LPD 16 may be configured to directly send a communication to SICD 30 that the tachyarrhythmia was not confirmed and that anti-tachyarrhythmia shock therapy is not advised. In some examples, LPD 16 may even communicate to SICD 30 the reason or reasons for not confirming the tachyarrhythmia. In other examples, LPD 16 may send a communication to SICD 30 that indicates the tachyarrhythmia was confirmed and ATP will not be delivered. The communication may even include the reason for not delivering ATP (e.g., the VT/VF was not pace terminable). In this case, SICD 30 may merely move to delivering the anti-tachyarrhythmia shock therapy.

SICD 30 may be configured to prepare to deliver anti-tachyarrhythmia shock therapy during delivery of ATP by LPD 16 and/or confirmation of the SICD detection of a tachyarrhythmia. For example, SICD 30 may be configured to charge a shock module (not shown in FIG. 1) of SICD 30 for delivery of a shock to patient 14. SICD 30 may also be configured to determine that the shock module is charged and ready for delivery of the anti-tachyarrhythmia shock therapy and, in response to the determination that the shock module is charged, deliver, via a set of electrodes of SICD 30, one or more shocks to patient 14. The set of electrodes for delivering the shock may include any electrodes of SICD 30, such as coil electrode 38 and housing 32 (when housing 32 is configured to be electrically conductive).

In some examples, SICD 30 may only deliver a shock to patient 14 if LPD 16 can confirm the SICD detection of a tachyarrhythmia. The confirmation from LPD 16 may be delivered in response to a request from SICD 30 or in response to independent detection of the tachyarrhythmia at LPD 16. For example, LPD 16 may be configured to determine that a sensed electrical signal comprises a tachyarrhythmia eligible for anti-tachyarrhythmia shock therapy and transmit communication to SICD 30 indicating the determination that the tachyarrhythmia eligible for anti-tachyarrhythmia shock therapy was detected. SICD 30 may then be configured to receive, from LPD 16, the communication indicating the determination that the sensed electrical signal at LPD 16 comprises the tachyarrhythmia eligible for anti-tachyarrhythmia shock therapy. In response to receiving the communication from LPD 16 indicating the determination, SICD 30 may deliver, via one or more electrodes of the SICD, anti-tachyarrhythmia shock therapy to patient 14.

SICD 30 may detect a tachyarrhythmia and determine to deliver a shock to patient 14 to treat the tachyarrhythmia. In some examples, SICD 30 may be configured to, in response to the determination to deliver the shock, transmit a communication requesting LPD 16 to deliver ATP. Delivery of ATP may be performed in an attempt to terminate the tachyarrhythmia prior to needing to deliver a shock. Since SICD 30 may require a period of time to charge prior to the SICD being capable of delivering the shock, the ATP may not even delay the delivery of the shock. Once SICD 30 requests that LPD 16 deliver ATP, SICD 30 may be configured to enter an ATP detection mode for detecting ATP therapy delivered by LPD 16. This ATP detection mode may allow SICD 30 to confirm that ATP was delivered and that LPD 16 also detected the tachyarrhythmia.

In addition, SICD 30 may be configured to analyze the ATP and intrinsic heart signals during the ATP detection mode to determine if the ATP therapy captured the heart rhythm. If capture was not achieved during ATP, SICD 30 may also be configured to transmit an instruction to LPD 16 that requests changing one or more parameter values that defines ATP. For example, in response to receiving a request from SICD 30 to deliver ATP, LPD 16 may deliver ATP to heart 12. SICD 30 may detect the delivered ATP therapy during the ATP detection mode and transmit communication identifying that the delivered ATP has not captured a rhythm of heart 12. In response to receiving the communication from SICD 30, LPD 16 may determine at least one updated parameter value that at least partially defines additional ATP for subsequent delivery to heart 12. Alternatively, SICD 30 may provide one or more updated parameter values for ATP based on the detected signals from heart 12 and LPD 16. In addition, SICD 30 may change one or more tachyarrhythmia detection criteria if ATP was not delivered by LPD 16 to increase the accuracy of SICD 30 arrhythmia detection. In response to SICD 30 detecting that LPD 16 delivered ATP to patient 14, SICD 30 may use this detection as confirmation that LPD 16 also detects the tachycardia.

As described above, LPD 16, SICD 30, or both, may be configured to initially detect arrhythmias. Since continued monitoring of ECGs requires processing power, system 10 may operate with only one device actively monitoring heart 12 for arrhythmias. The inactive device may be configured in a "sleep mode" or some other low power mode. The sleep mode may still maintain communication ability or some other protocol that allows the active device to "wake up" the inactive device. The inactive device may then become active to confirm detection of an arrhythmia and/or deliver therapy (e.g., anti-tachycardia therapy).

In one example, SICD 30 may be configured to continually monitor electrical signals of heart 12 for tachyarrhythmias. SICD 30 may detect, based on a sensed electrical signal, a tachyarrhythmia eligible for anti-tachyarrhythmia shock therapy and/or ATP. In response to this detection, SICD 30 may transmit communication to LPD 16 to sense electrical signals from heart 12 and determine if tachyarrhythmias are also detected with the sensing vectors of LPD 16. In this manner, SICD 30 may cause LPD 16 to "wake up" from an at least partially inactive state to an active state. LPD 16 may then transmit a communication to SICD 30 either confirming or denying the detection of a tachyarrhythmia. In some examples, LPD 16 may also begin delivery of ATP in response to detecting a tachyarrhythmia. LPD 16 may be set to inactive if it is not needed to treat conditions such as bradyarrhythmias in patient 14. However, if LPD 16 is required to monitor and/or treat bradyarrhythmias, LPD 16 may remain active to detect and/or treat tachyarrhythmias as well.

Alternatively, LPD 16 may be configured to detect, based on a sensed electrical signal, a tachyarrhythmia eligible for anti-tachyarrhythmia shock therapy, and, in response to the detection of the tachyarrhythmia, transmit communication requesting SICD 30 to sense electrical signals from heart 12 for tachyarrhythmias. This communication may cause SICD 30 to "wake up" from an at least partially inactive state to an active state. In response to receiving the communication from LPD 16, SICD 30 may be configured to sense electrical signals and determine whether any tachyarrhythmias are present in the electrical signals. SICD 30 may communicate with LPD 16 to confirm or deny the presence of tachyarrhythmias. In some examples, SICD 30 may immediately begin charging in response to also detecting a tachyarrhythmia. SICD 30 may also transmit a communication to LPD 16 confirming the arrhythmia detection and/or requesting LPD 16 to deliver ATP.

SICD 30 or LPD 16 may be used to continuously monitor heart 12 for arrhythmias for different reasons. For example, SICD 30 may include a higher capacity battery capable of supporting ECG monitoring for extended periods of time. In addition, patient 14 may benefit from monitoring with a far field ECG provided by electrodes 34, 38, and/or 40 of SICD 30. Alternatively, LPD 16 may be selected to continuously monitor heart 12 for arrhythmias due to the near-field ECG produced by electrodes within or near heart 12. In addition, electrical signals from heart 12 and detected at LPD 16 may have a higher signal-to-noise ratio. Moreover, although LPD 16 may include a lower capacity battery than that of SICD 30, LPD 16 may be less invasive for patient 14 and/or less expensive to replace than SICD 30.

In some examples, SICD 30 and/or LPD 16 may be configured to turn off or disable communication transmitters and/or receivers when they are not needed to conserve battery power. In response to detecting a tachyarrhythmia, SICD 30 and/or LPD 16 may turn on or enable the respective communication transmitters and/or receivers to perform one-way or two-way communication as described herein. In other words, SICD 30 and/or LPD 16 may not need to communicate with other devices unless patient 14 is experiencing a tachyarrhythmia, and communication services may be enabled on demand.

Although LPD 16 may at least partially determine whether or not LPD 16 delivers ATP or another therapy to patient 14, LPD 16 may perform one or more functions in response to receiving a request from SICD 30 and without any further analysis by LPD 16. In this manner, SICD 30 may act as a master device and LPD 16 may act as a slave device. In one example, SICD 30 may be configured to sense a first electrical signal from a heart of a patient and detect a tachyarrhythmia within the sensed first electrical signal. SICD 30 may then be configured to determine, based on the detected tachyarrhythmia, to deliver anti-tachyarrhythmia shock therapy to patient 14 to treat the detected arrhythmia. Prior to delivering the shock therapy, SICD 30 may be configured to transmit communication to LPD 16 requesting that LPD 16 deliver anti-tachycardia pacing to heart 12. LPD 16 may then receive the communication from SICD 30 requesting that the LPD deliver anti-tachycardia pacing to heart 12. In response to receiving the communication, LPD 16 may deliver, via one or more electrodes of the LPD, anti-tachycardia pacing to heart 12 of patient 14. In this example, LPD 16 may not be configured to withhold ATP once it has been requested by SICD 30.

In other examples, SICD 30 and LPD 16 may switch roles such that LPD 16 operates as the master device and SICD 30 operates as the slave device. For example, LPD 16 may analyze electrical signals and/or mechanical motions from heart 12 to detect tachyarrhythmias treatable by anti-tachyarrhythmia shock therapy. In response to detecting the anti-tachyarrhythmia, LPD 16 may transmit communication to SICD 30 requesting delivery of a shock. In response to receiving the communication from LPD 16, SICD 30 may charge and deliver a shock. Prior to delivery of the shock, LPD 16 may deliver ATP and/or enable to shock detector to identify when the shock is delivered to patient 14.

In addition to the delivery of ATP, LPD 16 may be configured to deliver post-shock pacing to heart 12. After delivery of an anti-tachyarrhythmia shock, heart 12 may benefit from pacing to return to a normal sinus rhythm (e.g., if heart 12 has developed bradycardia or asystole) or otherwise recover from receiving the shock. In some examples, LPD 16 and/or SICD 30 may be configured to detect bradycardia or asystole. In some examples, this post-shock pacing therapy may be automatically delivered in response to the LPD 16 detecting that a shock was delivered.

In one example, LPD 16 may be configured to receive an indication of a detected cardiac arrhythmia eligible for anti-tachyarrhythmia shock therapy. As described herein, LPD 16 may include a set of electrodes configured to be implanted within or near heart 12 of patient 14. In response to receiving the indication of the tachyarrhythmia, LPD 16 may enable a shock detector of LPD 16 configured to detect delivery of anti-tachyarrhythmia shock therapy. The shock detector may then detect delivery of anti-tachyarrhythmia shock therapy (e.g., detect that the shock has been delivered). In response to the detection of the shock, LPD 16 may deliver post-shock pacing therapy to heart 12 via at least a subset of the set of electrodes of LPD 16. In some examples, LPD 16 may deliver the post-shock pacing therapy after entering a post-shock pacing mode in response to detecting the shock. Alternatively, LPD 16 may use a timer to determine when a predetermined time has elapsed, during which the shock should have been delivered. LPD 16 may begin post-shock pacing after the predetermined period has elapsed.

LPD 16 may receive the indication of the detected cardiac arrhythmia in a variety of ways. For example, LPD 16 may sense, via at least a subset of the set of electrodes, an electrical signal from heart 12. LPD 16 may then detect, from the electrical signal, a cardiac arrhythmia eligible for anti-tachyarrhythmia shock therapy. In this manner, LPD 16 may receive the indication of the detected arrhythmia via direct detection of the arrhythmia at LPD 16. In another example, SICD 30 may be configured to transmit a communication including the indication to LPD 16. The indication of the detected arrhythmia may thus be received from SICD 30, for example. LPD 16 may receive a communication from SICD 30 indicating that a cardiac arrhythmia was detected by SICD 30. Alternatively, LPD 16 may receive a communication from SICD 30 merely indicating that a shock is impending. In other examples, LPD 16 may enable the shock detector when ATP is delivered to heart 12, in anticipation of a shock. In alternative examples, LPD 16 may enable the shock detector in response to detecting a fast rate, such as a tachyarrhythmia (e.g., when communication between LPD 16 and SICD 30 is not present or is unreliable). The tachyarrhythmia may be detected based on sensed electrical signals and/or mechanical signals from heart 12. In any example, the shock detector may be disabled until an indication of an arrhythmia is terminated or impending shock is received.

LPD 16 may also be configured to disable the shock detector. For example, LPD 16 may be configured to track a period of time following detection of delivery of anti-tachyarrhythmia shock therapy. The period of time may be a predetermined period of time and/or tracked with a timer, for example. LPD 16 may also determine that the period of time exceeds a timeout threshold, and, in response to the determination, disable the shock detector. LPD 16 may disable the shock detector when not needed to conserve battery power, for example.

LPD 16 may also re-start post shock pacing therapy if additional shocks are detected. For example, LPD 16 may be configured to detect a first shock and begin delivery of the post-shock pacing if needed (e.g., bradycardia or systole has been detected). LPD 16 may subsequently detect the delivery of a second shock, and, in response to the detection of the second shock, re-start delivery of the post-shock pacing therapy if needed. LPD 16 may continue to re-start post-shock pacing as long as additional shocks are delivered. However, LPD 16 may be configured to stop re-starting post-shock pacing after a predetermined number of shocks or SICD 30 transmits a message instructing LPD 16 to stop delivery of post-shock pacing. LPD 16 and/or SICD 30 may implement an intrinsic beat detector or other algorithm to distinguish between intrinsic beats and potential artifacts caused by pacing and/or shock therapy.

In some examples, LPD 16 may terminate post-shock pacing in response to various indicators. For example, LPD 16 may track a period of time following the start of post-shock pacing therapy. LPD 16 may then determine that the period of time exceeds a timeout threshold. For example, LPD 16 may use a timer to track this period of time. In response to the determination, LPD 16 may terminate delivery of post-shock pacing therapy. In other examples, LPD 16 may terminate post-shock pacing after delivery of a predetermined number of pacing pulses. Alternatively, LPD 16 may terminate post-shock pacing in response to detecting of a normal sinus rhythm or receiving a communication from SICD 30 instructing LPD 16 to terminate post-shock pacing.

Although LPD 16 is generally described as delivering post-shock pacing, in other examples, different implanted devices may provide post-shock pacing. For example, LPD 16 may be configured to deliver ATP, but a different LPD implanted in a different chamber of heart 12 may be configured to detect a shock and deliver the post-shock pacing to heart 12. In other examples, the implanted device delivering post-shock pacing may not be a leadless pacing device. For example, an implantable pacing device, separate from an ICD delivering the anti-tachyarrhythmia shock, may include one or more leads for delivering post-shock pacing pulses to one or more locations of heart 12.

Figure 2A:
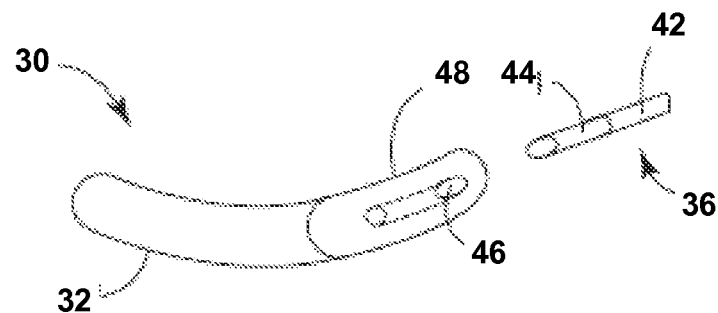
FIGS. 2A and 2B are conceptual drawings illustrating different views of the example SICD of FIG. 1
Figure 2B:
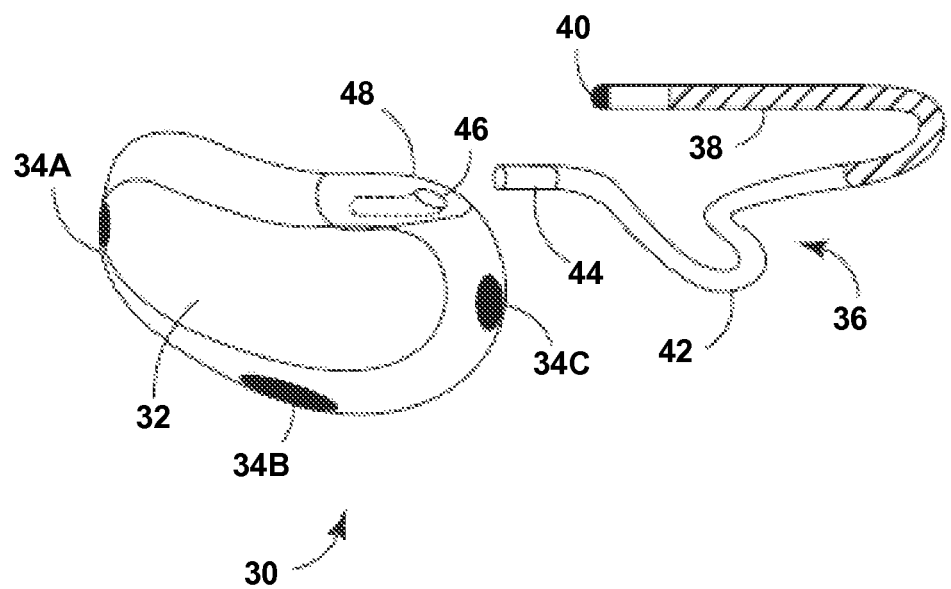

FIGS. 2A and 2B are conceptual drawings illustrating different views of SICD 30 of FIG. 1. FIG. 2A is a top view of SICD 30, and FIG. 2B is a front view of SICD 30. In the example of FIGS. 2A and 2B, housing 32 may be constructed as an ovoid with a substantially kidney-shaped profile. The ovoid shape of housing 32 may promote ease of subcutaneous implantation and may minimize patient discomfort during normal body movement and flexing of the thoracic musculature. In other examples, housing 32 may be constructed with different shapes intended for different implant locations and/or to house different components, subcutaneous leads, or configurations for electrodes 34 FIG. 2B.

Housing 32 may contain the electronic circuitry of SICD 30. Header 48 and connector 46 may provide an electrical connection between distal electrode coil 38 and distal sensing electrode 40 of lead 36 and the circuitry within housing 32. Subcutaneous lead 36 may include distal defibrillation coil electrode 38, distal sensing electrode 40, insulated flexible lead body 42 and proximal connector pin 44. Distal sensing electrode 40 may be sized appropriately to match the sensing impedance of electrodes 34A-34C to be used in combination.

In some examples, electrodes 34 are each welded into place on a flattened periphery of housing 32 and are connected to electronic circuitry inside housing 32. Electrodes 34 may be constructed of flat plates, or alternatively, spiral electrodes (as described in U.S. Pat. No. 6,512,940, incorporated herein in its entirety) and mounted in a non-conductive surround shroud (as described in U.S. Pat. Nos. 6,522,915 and 6,622,046, both incorporated herein in their entirety). Electrodes 34 shown in FIG. 2B may be positioned on housing 32 to form orthogonal signal vectors. However, electrodes 34 may be positioned to form any non-orthogonal signal vectors in other examples. In addition, housing 32 may include fewer or greater than three electrodes. Moreover, housing 32 may be configured as an electrically conductive surface and operate as an electrode. Housing 32 may be referred to as a "can electrode" or used as an indifferent electrode. In some examples, housing 32 may be used as an electrode with coil electrode 38 during delivery of an anti-tachyarrhythmia shock.

In other examples, housing 32 may be coupled to a second subcutaneous lead extending away from housing 32 in the opposite direction of lead 36. In this manner, the second subcutaneous lead may carry one or more of electrodes 34. Housing 32 may alternatively be coupled to three or more subcutaneous leads. In other examples, lead 36 may be formed as an extension of housing 32 such that SICD 30 comprises an elongated housing to carry electrodes 34, 38, and 40 without any leads (e.g., lead 36.

Figure 3:
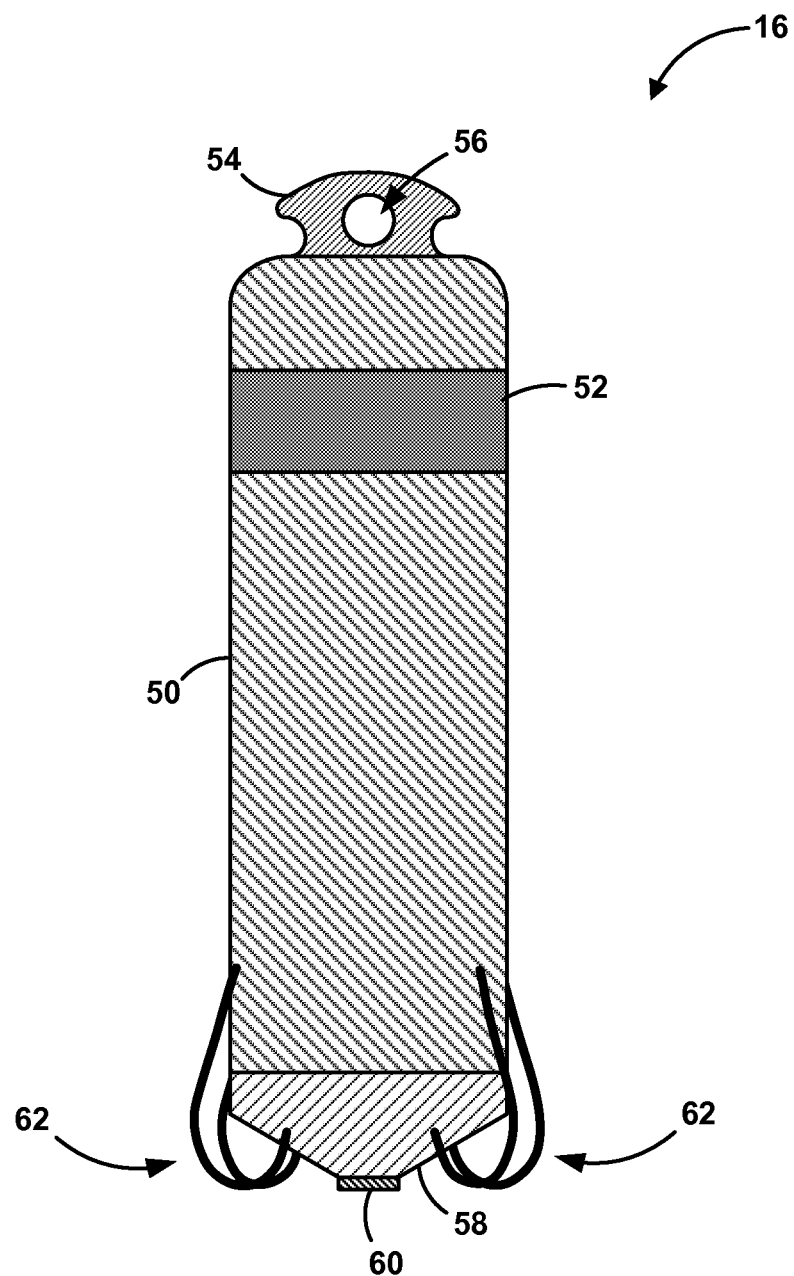
FIG. 3 is a conceptual drawing illustrating the example LPD of FIG. 1.

FIG. 3 is a conceptual drawing illustrating example LPD 16 of FIG. 1. As shown in FIG. 3, LPD 16 includes case 50, cap 58, electrode 60, electrode 52, fixation mechanisms 62, flange 54, and opening 56. Together, case 50 and cap 58 may be considered the housing of LPD 16. In this manner, case 50 and cap 58 may enclose and protect the various electrical components within LPD 16. Case 50 may enclose substantially all of the electrical components, and cap 58 may seal case 50 and create the hermetically sealed housing of LPD 16. Although LPD 16 is generally described as including one or more electrodes, LPD 16 may typically include at least two electrodes (e.g., electrodes 52 and 60) to deliver an electrical signal (e.g., therapy such as ATP) and/or provide at least one sensing vector.

Electrodes 52 and 60 are carried on the housing created by case 50 and cap 58. In this manner, electrodes 52 and 60 may be considered leadless electrodes. In the example of FIG. 3, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating. Electrode 60 may be used as a cathode and electrode 52 may be used as an anode, or vise versa, for delivering pacing stimulation therapy such as ATP or post-shock pacing. However, electrodes 52 and 60 may be used in any stimulation configuration. In addition, electrodes 52 and 60 may be used to detect intrinsic electrical signals from cardiac muscle. In other examples, LPD 16 may include three or more electrodes, where each electrode may deliver therapy and/or detect intrinsic signals. ATP delivered by LPD 16 may be considered to be "painless" to patient 14 or even undetectable by patient 14 since the electrical stimulation occurs very close to or at cardiac muscle and at relatively low energy levels compared with alternative devices.

Fixation mechanisms 62 may attach LPD 16 to cardiac tissue. Fixation mechanisms 62 may be active fixation tines, screws, clamps, adhesive members, or any other types of attaching a device to tissue. As shown in the example of FIG. 3, fixation mechanisms 62 may be constructed of a memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of LPD 16. For example, a suture or other device may be inserted around flange 54 and/or through opening 56 and attached to tissue. In this manner, flange 54 may provide a secondary attachment structure to tether or retain LPD 16 within heart 12 if fixation mechanisms 62 fail. Flange 54 and/or opening 56 may also be used to extract LPD 16 once the LPD needs to be explanted (or removed) from patient 14 if such action is deemed necessary.

The techniques described herein are generally described with regard to a leadless pacing device such as LPD 16. LPD 16 may be an example of an anti-tachycardia pacing device (ATPD). However, alternative implantable medical devices may be used to perform the same or similar functions as LPD 16 (e.g., delivering ATP to heart 12) and communicate with SICD 30. For example, an ATPD may include a small housing that carries an electrode, similar to LPD 16, and configured to be implanted within a chamber of heart 12. The ATPD may also include one or more relatively short leads configured to place one or more respective additional electrodes at another location within the same chamber of the heart or a different chamber of the heart. This configuration may be referred to as an Intercardiac Pacing Device (IPD). In this manner, the housing of the ATPD may not carry all of the electrodes used to deliver ATP or perform other functions. In other examples, each electrode of the ATPD may be carried by one or more leads (e.g., the housing of the ATPD may not carry any of the electrodes).

In another example, the ATPD may be configured to be implanted external to heart 12, e.g., near or attached to the epicardium of heart 12. An electrode carried by the housing of the ATPD may be placed in contact with the epicardium and/or one or more electrodes of leads coupled to the ATPD may be placed in contact with the epicardium at locations sufficient to provide therapy such as ATP (e.g., on external surfaces of the left and/or right ventricles). In any example, SICD 30 may communicate with one or more leadless or leaded devices implanted internal or external to heart 12.

Figure 4:
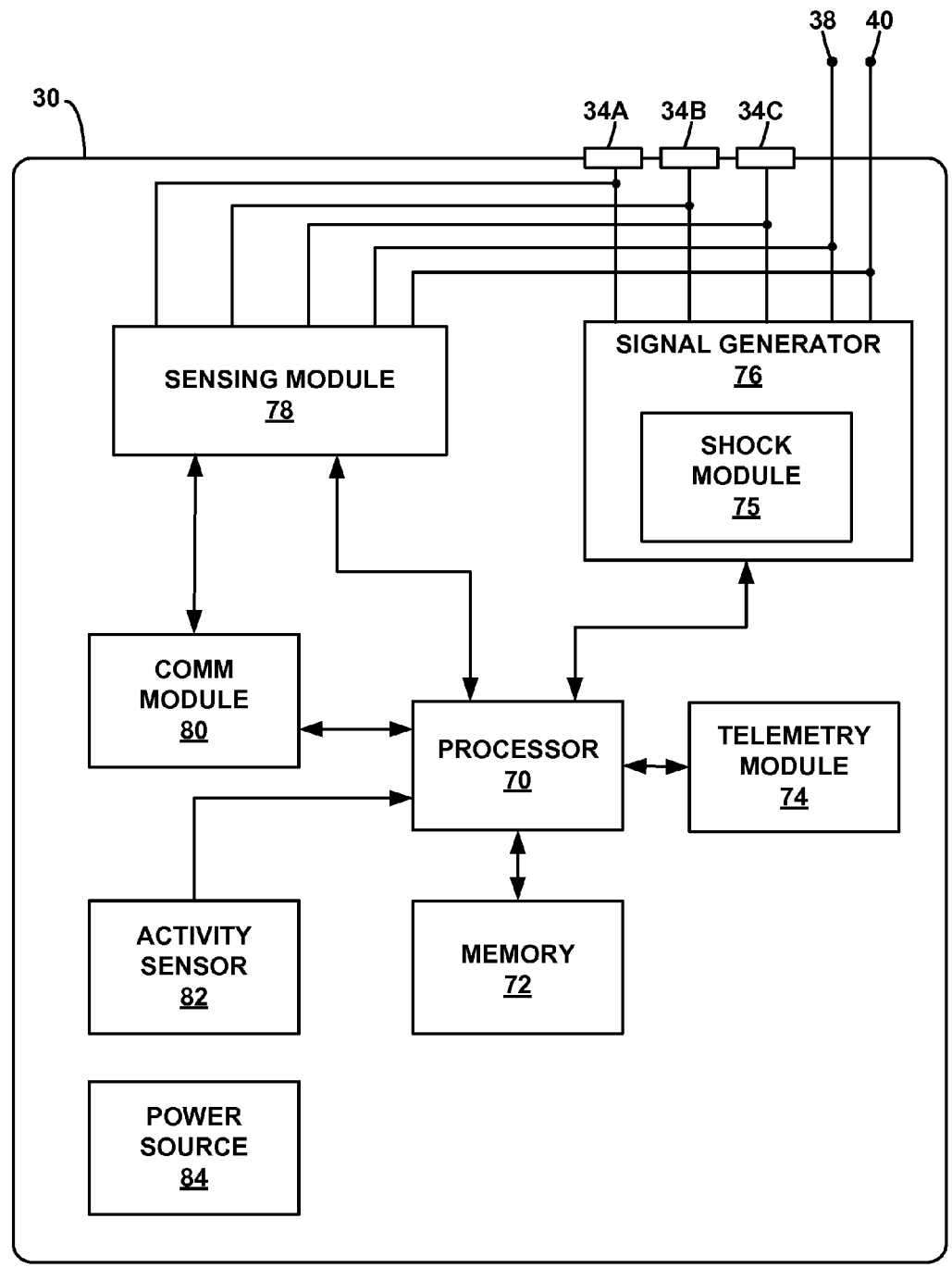
FIG. 4 is a functional block diagram illustrating an example configuration of the SICD of FIG. 1.

FIG. 4 is a functional block diagram illustrating an example configuration of SICD 30 of FIG. 1. In the illustrated example, SICD 30 includes a processor 70, memory 72, shock module 75, signal generator 76, sensing module 78, telemetry module 74, communication module 80, activity sensor 82, and power source 84. Memory 72 includes computer-readable instructions that, when executed by processor 70, cause SICD 30 and processor 70 to perform various functions attributed to SICD 30 and processor 70 herein (e.g., detection of tachyarrhythmias, communication with LPD 16, and/or delivery of anti-tachyarrhythmia shock therapy). Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Processor 70 controls signal generator 76 to deliver stimulation therapy to heart 12 according to a therapy parameters, which may be stored in memory 72. For example, processor 70 may control signal generator 76 to deliver electrical pulses (e.g., shock pulses) with the amplitudes, pulse widths, frequency, or electrode polarities specified by the therapy parameters. In this manner, signal generator 76 may deliver electrical pulses to heart 12 via electrodes 34, 38, and/or 40. In addition, housing 30 may be configured as an electrode and coupled to signal generator 76 and/or sensing module 78. SICD 30 may use any combination of electrodes to deliver anti-tachycardia therapy and/or detect electrical signals from patient 14. However, in general, coil electrode 38 may be used to deliver an anti-tachyarrhythmia shock.

Signal generator 76 may also include shock module 75. Shock module 75 may include circuitry and/or capacitors required to deliver an anti-tachyarrhythmia shock. For example, signal generator 76 may charge shock module 75 to prepare for delivering a shock. Shock module 75 may then discharge to enable signal generator 76 to deliver the shock to patient 14 via one or more electrodes. In other examples, shock module 75 may be located within SICD 30 but outside of signal generator 76.

Signal generator 76 is electrically coupled to electrodes 34, 38, and 40. In the illustrated example, signal generator 76 is configured to generate and deliver electrical anti-tachyarrhythmia shock therapy to heart 12. For example, signal generator 76 may, using shock module 75, deliver shocks to heart 12 via a subset of electrodes 34, 38, and 40. In some examples, signal generator 76 may deliver pacing stimulation, and cardioversion or defibrillation shocks in the form of electrical pulses. In other examples, signal generator may deliver one or more of these types of stimulation or shocks in the form of other signals, such as sine waves, square waves, or other substantially continuous time signals.

Signal generator 76 may include a switch module and processor 70 may use the switch module to select, e.g., via a data/address bus, which of the available electrodes are used to deliver shock and/or pacing pulses. The switch module may include a switch array, switch matrix, multiplexer, or any other type of switching device suitable to selectively couple stimulation energy to selected electrodes.

Electrical sensing module 78 may be configured to monitor signals from at least one of electrodes 34, 38, and 40 in order to monitor electrical activity of heart 12, impedance, or other electrical phenomenon. Sensing may be done to determine heart rates or heart rate variability, or to detect arrhythmias (e.g., tachyarrhythmia) or other electrical signals. Sensing module 78 may also include a switch module to select which of the available electrodes are used to sense the heart activity, depending upon which electrode combination, or electrode vector, is used in the current sensing configuration. In examples with several electrodes, processor 70 may select the electrodes that function as sense electrodes, i.e., select the sensing configuration, via the switch module within sensing module 78. Sensing module 78 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 70, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 70 may control the functionality of sensing module 78 by providing signals via a data/address bus.

Processor 70 may include a timing and control module, which may be embodied as hardware, firmware, software, or any combination thereof. The timing and control module may comprise a dedicated hardware circuit, such as an ASIC, separate from other processor 70 components, such as a microprocessor, or a software module executed by a component of processor 70, which may be a microprocessor or ASIC. The timing and control module may implement programmable counters. If SICD 30 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 70 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 78 for a time interval during and after delivery of electrical stimulation to heart 12. The durations of these intervals may be determined by processor 70 in response to stored data in memory 72. The timing and control module of processor 70 may also determine the amplitude of the cardiac pacing pulses.

Interval counters implemented by the timing and control module of processor 70 may be reset upon sensing of R-waves and P-waves with detection channels of sensing module 78. The value of the count present in the interval counters when reset by sensed R-waves and P-waves may be used by processor 70 to measure the durations of R-R intervals, P-P intervals, P-R intervals and R-P intervals, which are measurements that may be stored in memory 72. Processor 70 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 72 may be configured as a plurality of recirculating buffers, capable of holding series of measured intervals, which may be analyzed by processor 70 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processor 70 in other examples.

In some examples, processor 70 may determine that tachyarrhythmia has occurred by identification of shortened R-R (or P-P) interval lengths. Generally, processor 70 detects tachycardia when the interval length falls below 220 milliseconds (ms) and fibrillation when the interval length falls below 180 ms. In other examples, processor 70 may detect ventricular tachycardia when the interval length falls between 330 ms and ventricular fibrillation when the interval length falls between 240 ms. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In the event that processor 70 detects an atrial or ventricular tachyarrhythmia based on signals from sensing module 78, and an anti-tachyarrhythmia pacing regimen is desired, timing intervals for controlling the generation of anti-tachyarrhythmia pacing therapies by signal generator 76 may be loaded by processor 70 into the timing and control module to control the operation of the escape interval counters therein and to define refractory periods during which detection of R-waves and P-waves is ineffective to restart the escape interval counters for the an anti-tachyarrhythmia pacing. In addition to detecting and identifying specific types of cardiac rhythms (types of cardiac events), sensing module 78 may also sample the detected intrinsic signals to generate an electrogram or other time-based indication of cardiac events.

In some examples, communication module 80 may be used to detect communication signals from LPD 16. LPD 16 may not include telemetry circuitry. Instead, LPD 16 may generate electrical signals via one or more electrodes with amplitudes and/or patterns representative of information to be sent to SICD 30. The electrical signals may be carried by pacing pulses or separate communication signals configured to be detected by SICD 30. In this manner, communication module 80 may be configured to monitor signals sensed by sensing module 78 and determine when a communication message is received from LPD 16.

In other examples, SICD 30 may also transmit communication messages to LPD 16 using electrical signals from one or more of electrodes 34, 38, and 40. In this case, communication module 80 may be coupled to signal generator 76 to control the parameters of generated electrical signals or pulses. Alternatively, processor 70 may detect communications via sensing module 78 and/or generate communications for deliver via signal generator 76. Although communication module 80 may be used to communicate using electrical signals via electrodes 34, 38 and 40, communication module 80 may alternatively or in addition use wireless protocols such as RF telemetry to communicate with LPD 16 or other medical devices. In some examples, telemetry module 74 may include this wireless communication functionality.

Memory 72 may be configured to store a variety of operational parameters, therapy parameters, sensed and detected data, and any other information related to the monitoring, therapy and treatment of patient 14. Memory 72 may store, for example, thresholds and parameters indicative of tachyarrhythmias and/or therapy parameter values that at least partially define delivered anti-tachyarrhythmia shocks. In some examples, memory 72 may also store communications transmitted to and/or received from LPD 16.

Activity sensor 82 may be contained within the housing of SICD 30 and include one or more accelerometers or other devices capable of detecting motion and/or position of SICD 30. For example, activity sensor 82 may include a 3-axis accelerometer that is configured to detect accelerations in any direction in space. Accelerations detected by activity sensor 82 may be used by processor 70 to identify potential noise in signals detected by sensing module 78 and/or confirm the detection of arrhythmias or other patient conditions.

Telemetry module 74 includes any suitable hardware, firmware, software or any combination thereof for communicating with another device, such as programmer 20 (FIG. 1). As described herein, telemetry module 74 may transmit generated or received arrhythmia data, therapy parameter values, communications between SICD 30 and LPD 16, or any other information. For example, telemetry module 74 may transmit information representative of sensed physiological data such as R-R intervals or any other data that may be used by LPD 16 to determine a condition of patient 14. Telemetry module 74 may also be used to receive updated therapy parameters from programmer 20. Under the control of processor 70, telemetry module 74 may receive downlink telemetry from and send uplink telemetry to programmer 20 with the aid of an antenna, which may be internal and/or external. Processor 70 may provide the data to be uplinked to programmer 20 and the control signals for the telemetry circuit within telemetry module 74, e.g., via an address/data bus. In some examples, telemetry module 74 may provide received data to processor 70 via a multiplexer.

In some examples, SICD 30 may signal programmer 20 to further communicate with and pass the alert through a network such as the Medtronic CareLink® Network developed by Medtronic, Inc., of Minneapolis, Minn., or some other network linking patient 14 to a clinician. SICD 30 may spontaneously transmit the diagnostic information to the network or in response to an interrogation request from a user.

Power source 84 may be any type of device that is configured to hold a charge to operate the circuitry of SICD. Power source 84 may be provided as a rechargeable or non-rechargeable battery. In other examples, power source 84 may also incorporate an energy scavenging system that stores electrical energy from movement of SICD 30 within patient 14.

There may be numerous variations to the configuration of SICD 30, as described herein. In the examples of FIGS. 2A, 2B, and 4, SICD 30 may include housing 32 configured to be implanted in patient 14 external to a rib cage of patient 14, one or more electrodes (e.g., electrodes 34, 38, and 40) configured to be disposed external to the rib cage, and shock module 75 configured to at least partially deliver anti-tachyarrhythmia shock therapy to patient 14 via the one or more electrodes. By at least partially delivering anti-tachyarrhythmia shock therapy, one or more components, in addition to shock module 75, may be considered as contributing to the delivery of the anti-tachyarrhythmia shock therapy. SICD 30 may also include communication module 80 configured to transmit and/or receive communication messages between LPD 16 configured to be implanted within heart 12 of patient 14 and a sensing module 78 configured to sense an electrical signal from heart 12 of patient 14 via the one or more electrodes. Further, SICD 30 may include one or more processors 70 configured to detect a tachyarrhythmia within the sensed electrical signal and determine, based on the detected tachyarrhythmia, to deliver anti-tachyarrhythmia shock therapy to patient 14 to treat the detected tachyarrhythmia. Processor 70 may also be configured to transmit, via communication module 80 and prior to delivering anti-tachyarrhythmia shock therapy, a communication message to LPD 16 requesting LPD 16 deliver ATP to heart 12 of patient 14.

Figure 5:
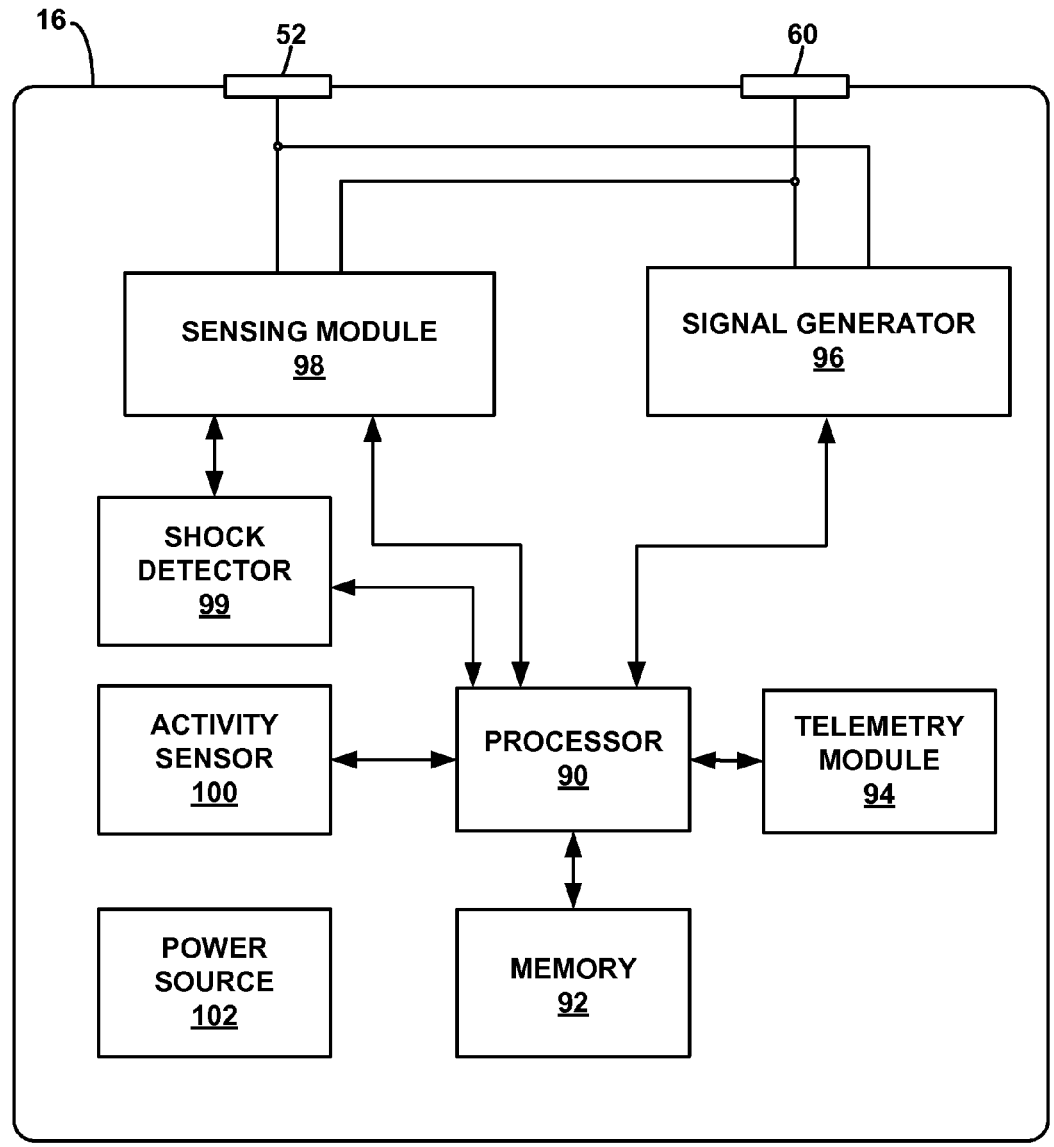
FIG. 5 is a functional block diagram illustrating an example configuration of the LPD of FIG. 1.

FIG. 5 is a functional block diagram illustrating an example configuration of LPD 16 of FIG. 1. In the illustrated example, LPD 16 includes a processor 90, memory 92, signal generator 96, sensing module 98, shock detector 99, activity sensor 100, telemetry module 94, and power source 102. Memory 92 includes computer-readable instructions that, when executed by processor 90, cause LPD 16 and processor 90 to perform various functions attributed to LPD 16 and processor 90 herein (e.g., detecting arrhythmias, communicating with SICD 30, and delivering anti-tachycardia pacing and post-shock pacing). Memory 92 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 90 may include any one or more of a microprocessor, a controller, a digital signal processor (DSP), an application specific integrated circuit (ASIC), a field-programmable gate array (FPGA), or equivalent discrete or analog logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processor 90 herein may be embodied as software, firmware, hardware or any combination thereof.

Processor 90 controls signal generator 96 to deliver stimulation therapy to heart 12 according to a therapy parameters, which may be stored in memory 92. For example, processor 90 may control signal generator 96 to deliver electrical pulses with the amplitudes, pulse widths, frequency, or electrode polarities specified by the therapy parameters. In this manner, signal generator 96 may deliver pacing pulses (e.g., ATP pulses or post-shock pacing pulses) to heart 12 via electrodes 52 and 60. Although LPD 16 may only include two electrodes, e.g., electrodes 52 and 60, LPD 16 may utilize three or more electrodes in other examples. LPD 16 may use any combination of electrodes to deliver therapy and/or detect electrical signals from patient 14.

Signal generator 96 is electrically coupled to electrodes 52 and 60 carried on the housing of LPD 16. In the illustrated example, signal generator 96 is configured to generate and deliver electrical stimulation therapy to heart 12. For example, signal generator 96 may deliver ATP pulses to a portion of cardiac muscle within heart 12 via electrodes 52 and 60. In some examples, signal generator 96 may deliver pacing stimulation in the form of electrical pulses. In other examples, signal generator may deliver one or more of these types of stimulation in the form of other signals, such as sine waves, square waves, or other substantially continuous time signals. Although LPD 16 is generally described has delivering pacing pulses, LPD 16 may deliver cardioversion or defibrillation pulses in other examples.

ATP may be delivered to patient 14 as defined by a set of parameters. These parameters may include pulse intervals, pulse width, current and/or voltage amplitudes, and durations for each pacing mode. For example, the pulse interval may be between approximately 150 milliseconds (ms) and 500 (ms) (e.g., between approximately 2.0 Hz and 7.0 Hz), and the pulse width may be between approximately 1.0 ms and 2.0 ms. The amplitude of each pacing pulse may be between approximately 2.0 Volts (V) and 10.0 V, such as approximately 6.0 V. In some examples, the pulse amplitude may be approximately 6.0 V and the pulse width may be approximately 1.5 ms; another example may include pulse amplitudes of approximately 5.0 V and pulse widths of approximately 1.0 ms. Each train of pulses during ATP may last for a duration of between approximately 0.5 seconds to approximately 15 seconds. Each pulse, or burst of pulses, may include a ramp up in amplitude. In addition, trains of pulses in successive ATP periods may in delivered at increasing pulse rate in an attempt to capture the heart and terminate the tachycardia. Example ATP parameters and other criteria involving the delivery of ATP are described in U.S. Pat. No. 6,892,094 to Ousdigian et al., entitled, "COMBINED ANTI-TACHYCARDIA PACING (ATP) AND HIGH VOLTAGE THERAPY FOR TREATING VENTRICULAR ARRHYTHMIAS," and issued on May 10, 2005, the entire content of which is incorporated herein by reference.

Parameters than define post-shock pacing may also vary based on the type of tachyarrhythmias detected after the shock. In one example of biphasic pulses, post-shock pacing pulses may have a pulse width of approximately 7 ms at each phase and a pulse amplitude of approximately 200 mA. The duration of each post-shock pacing period may be between 10 seconds and 60 seconds, or even longer in other examples. In other examples, pulse widths, pulse amplitudes, and/or durations of post-shock pacing may be greater or lower.

Signal generator 96 may also include circuitry for measuring the capture threshold of one or both electrodes 52 and 60. The capture threshold may indicate the voltage necessary to induce depolarization of the surrounding cardiac muscle. For example, signal generator 96 may measure the voltage of pacing signals needed to induce ventricular contractions. In examples in which LPD 16 includes more than two electrodes, signal generator 96 may include a switch module and processor 90 may use the switch module to select, e.g., via a data/address bus, which of the available electrodes are used to deliver pacing pulses. The switch module may include a switch array, switch matrix, multiplexer, or any other type of switching device suitable to selectively couple stimulation energy to selected electrodes. In the instance that the capture threshold exceeds useable limits, processor 90 may withhold delivery of ATP or post-shock pacing. In addition, processor 90 may transmit communication to SICD 30 if pacing cannot be delivered.

Electrical sensing module 98 monitors signals from at least one of electrodes 52 and 60 in order to monitor electrical activity of heart 12, impedance, or other electrical phenomenon. Sensing may be done to determine heart rates or heart rate variability, or to detect arrhythmias (e.g., tachyarrhythmias) or other electrical signals. Sensing module 98 may also include a switch module to select which of the available electrodes (or electrode polarity) are used to sense the heart activity, depending upon which electrode combination, or electrode vector, is used in the current sensing configuration. In examples with several electrodes, processor 90 may select the electrodes that function as sense electrodes, i.e., select the sensing configuration, via the switch module within sensing module 98. Sensing module 98 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 90, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 90 may control the functionality of sensing module 98 by providing signals via a data/address bus.

Processor 90 may include a timing and control module, which may be embodied as hardware, firmware, software, or any combination thereof. The timing and control module may comprise a dedicated hardware circuit, such as an ASIC, separate from other processor 90 components, such as a microprocessor, or a software module executed by a component of processor 90, which may be a microprocessor or ASIC. The timing and control module may implement programmable counters. If LPD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing. Example LPDs that may deliver pacing using such modes are described in U.S. patent application Ser. No. 13/665,492 to Bonner et al., entitled, "LEADLESS PACEMAKER SYSTEM," and filed on Oct. 31, 2012, or in U.S. patent application Ser. No. 13/665,601 to Bonner et al., entitled, "LEADLESS PACEMAKER SYSTEM," and filed on Oct. 31, 2012. U.S. patent application Ser.

No. 13/665,492 to Bonner et al. and U.S. patent Ser. No. 13/665,601 to Bonner et al. are both incorporated herein by reference in their entireties.

Intervals defined by the timing and control module within processor 90 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 98 for a time interval during and after delivery of electrical stimulation to heart 12. The durations of these intervals may be determined by processor 90 in response to stored data in memory 92. The timing and control module of processor 90 may also determine the amplitude of the cardiac pacing pulses.

Interval counters implemented by the timing and control module of processor 90 may be reset upon sensing of R-waves and P-waves with detection channels of sensing module 98. In examples in which LPD 16 provides pacing, signal generator 96 may include pacer output circuits that are coupled to electrodes 34 and 46, for example, appropriate for delivery of a bipolar or unipolar pacing pulse to one of the chambers of heart 12. In such examples, processor 90 may reset the interval counters upon the generation of pacing pulses by signal generator 96, and thereby control the basic timing of cardiac pacing functions, including ATP or post-shock pacing.

The value of the count present in the interval counters when reset by sensed R-waves and P-waves may be used by processor 90 to measure the durations of R-R intervals, P-P intervals, P-R intervals and R-P intervals, which are measurements that may be stored in memory 92. Processor 90 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 92 may be configured as a plurality of recirculating buffers, capable of holding series of measured intervals, which may be analyzed by processor 90 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 90 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies, such as those methodologies that utilize timing and morphology of the electrocardiogram, may also be employed by processor 90 in other examples.

In some examples, processor 90 may determine that tachyarrhythmia has occurred by identification of shortened R-R (or P-P) interval lengths. Generally, processor 90 detects tachycardia when the interval length falls below 220 milliseconds (ms) and fibrillation when the interval length falls below 180 ms. In other examples, processor 70 may detect ventricular tachycardia when the interval length falls between 330 ms and ventricular fibrillation when the interval length falls between 240 ms. These interval lengths are merely examples, and a user may define the interval lengths as desired, which may then be stored within memory 92. This interval length may need to be detected for a certain number of consecutive cycles, for a certain percentage of cycles within a running window, or a running average for a certain number of cardiac cycles, as examples. In other examples, additional physiological parameters may be used to detect an arrhythmia. For example, processor 90 may analyze one or more morphology measurements, impedances, or any other physiological measurements to determine that patient 14 is experiencing a tachyarrhythmia.

In the event that processor 90 detects an atrial or ventricular tachyarrhythmia based on signals from sensing module 98, and an ATP regimen is desired, timing intervals for controlling the generation of ATP therapies by signal generator 96 may be loaded by processor 90 into the timing and control module to control the operation of the escape interval counters therein and to define refractory periods during which detection of R-waves and P-waves is ineffective to restart the escape interval counters for the ATP.

In addition to detecting and identifying specific types of cardiac rhythms (types of cardiac events), sensing module 98 may also sample the detected intrinsic signals to generate an electrogram or other time-based indication of cardiac events. Processor 90 may also be able to coordinate the delivery of pacing pulses from different LPDs implanted in different chambers of heart 12, such as an LPD implanted in atrium 22 and/or an LPD implanted in left ventricle 24. For example, processor 90 may identify delivered pulses from other LPDs via sensing module 98 and updating pulse timing to accomplish a selected pacing regimen. This detection may be on a pulse-to-pulse or beat-to-beat basis or on a less frequent basis to make slight modifications to pulse rate over time. In other examples, LPDs may communicate with each other via telemetry module 94 and/or instructions over a carrier wave (such as a stimulation waveform). In this manner, ATP or post-shock pacing may be coordinated from multiple LPDs.

Shock detector 99 may be used to detect anti-tachyarrhythmia shocks delivered by SICD 30 or another device. For example, processor 90 may enable shock detector 99 in response to detecting a tachyarrhythmia or receiving a communication indicating that an arrhythmia has been detected or a shock is imminent. Processor 90 may also disable shock detector 99 after a predetermined time period has elapsed or a shock is otherwise not anticipated. When shock detector 99 is enabled, shock detector 99 may identify with an electric signal received by sensing module 98 is representative of an artificial cardioversion or defibrillation shock pulse.

In response to detecting a shock via shock detector 99, processor 90 may begin post-shock pacing when such functionality has been enabled for therapy. Processor 90 may also re-start post-shock pacing in response to detecting additional shocks via shock detector 99. In some examples, processor 90 may terminate ATP upon detection of a shock.

Memory 92 may be configured to store a variety of operational parameters, therapy parameters, sensed and detected data, and any other information related to the therapy and treatment of patient 14. In the example of FIG. 5, memory 92 may store sensed ECGs, detected arrhythmias, communications from SICD 30, and therapy parameters that define ATP and/or post-shock pacing regimens. In other examples, memory 92 may act as a temporary buffer for storing data until it can be uploaded to SICD 30, another implanted device, or programmer 20.

Activity sensor 100 may be contained within the housing of LPD 16 and include one or more accelerometers or other devices capable of detecting motion and/or position of LPD 16. For example, activity sensor 100 may include a 3-axis accelerometer that is configured to detect accelerations in any direction in space. Specifically, the 3-axis accelerator may be used to detect LPD 16 motion that may be indicative of cardiac events and/or noise. For example, processor 16 may monitor the accelerations from activity sensor 100 to confirm or detect arrhythmias. Since LPD 16 may move with a chamber wall of heart 12, the detected changes in acceleration may also be indicative of contractions. Therefore, LPD 16 may be configured to identify heart rates and confirm arrhythmias, such as a tachycardia, sensed via sensing module 98.

Telemetry module 94 includes any suitable hardware, firmware, software or any combination thereof for communicating with another device, such as programmer 20 or SICD 30 (FIG. 1). Under the control of processor 90, telemetry module 94 may receive downlink telemetry from and send uplink telemetry to programmer 20 with the aid of an antenna, which may be internal and/or external. Processor 90 may provide the data to be uplinked to programmer 20 and the control signals for the telemetry circuit within telemetry module 94, e.g., via an address/data bus. In some examples, telemetry module 94 may provide received data to processor 90 via a multiplexer.

In some examples, LPD 16 may signal programmer 20 to further communicate with and pass the alert through a network such as the Medtronic CareLink® Network developed by Medtronic, Inc., of Minneapolis, Minn., or some other network linking patient 14 to a clinician. LPD 16 may spontaneously transmit information to the network or in response to an interrogation request from a user.

In other examples, processor 90 may be configured to transmit information to another device, such as SICD 30 using electrodes 52 and 60. For example, processor 90 may control signal generator 96 to generate electrical signals representative of commands such as the detection of an arrhythmia, confirmation that a tachycardia has been detected, a request to monitor electrical signals for arrhythmias, or even signals to "wake up" an SICD in a sleep mode. In other examples, processor 90 may cause telemetry module 94 to transmit information representative of sensed physiological data such as R-R intervals or any other data that may be used by SICD 30 to determine a condition of patient 14 (e.g., whether or not patient 14 is experiencing an arrhythmia). The communication may be in the form of dedicated communication signals.

Alternatively, processor 90 may communicate with SICD 30 by delivering pacing pulses at specific intervals that would be identifiable by SICD 30 as non-physiologic and intended to convey information. In other words, these pulses intended for communication with SICD 30. SICD 30 may be configured to identify, or distinguish, these pulses from signals indicative of normal or non-normal heart beats, signals indicative of ectopic or non-ectopic heart beats, signals indicative of noise (e.g., lead fracture noise or skeletal muscle noise), or any other signals indicative of typically physiological or therapeutic electrical signals. The communication pulses may or may not be ATP pulses or other therapeutic pulses or signals. SICD 30 may detect the intervals between these pulses as code for specific messages from LPD 16. For example, the pacing pulses may be varied and/or repeated in certain patterns detectable by SICD 30 and still therapeutic. Example variation of pacing rate may be a string of groups of 10 pulses at changing rates of 100 pulses per minute (ppm), 110 ppm, 105 ppm, 100 ppm, 110 ppm, 105 ppm, etc. In some examples, pulses intended for communication may be delivered during an electrophysiologic refractory period to avoid potential cardiac capture. LPD 16 may also be configured to detect such communication messages via electrodes 52 and 60. Processor 90 may monitor sensing module 98 for such communications. Alternatively, LPD 16 may include a communication module, similar to communication module 80 of FIG. 4, to detect any communications received via sensing module 98. In any example, LPD 16 may be configured for one-way communication to or from another device such as SICD 30 or two-way communication with another device such as SICD 30 using any type of communication protocol.

Power source 102 may be any type of device that is configured to hold a charge to operate the circuitry of LPD 16. Power source 102 may be provided as a rechargeable or non-rechargeable battery. In other example, power source 102 may incorporate an energy scavenging system that stores electrical energy from movement of LPD 16 within patient 14.

There may be numerous variations to the configuration of LPD 16, as described herein. In one example, LPD 16 includes a housing configured to be implanted within heart 12 of patient 14, one or more electrodes (e.g., electrodes 52 and 60) coupled to the housing, fixation mechanism 62 configured to attach the housing to tissue of heart 12, sensing module 98 configured to sense an electrical signal from heart 12 of patient 14 via the one or more electrodes, and signal generator 96 configured to deliver ATP therapy to heart 12 of patient 14 via the one or more electrodes. LPD 16 may also include processor 90 configured to receive a communication message from SICD 30 requesting LPD 16 deliver ATP to heart 12, where SICD 30 is configured to be implanted exterior to a rib cage of patient 14. Processor 90 may also be configured to determine, based on the sensed electrical signal, whether to deliver ATP to heart 12, and, in response to the determination, command signal generator 96 to deliver the ATP therapy. Processor 90 may also be configured to control signal generator 96 to deliver post-shock pacing to patient 14 in response to shock detector 99 detecting an anti-tachyarrhythmia shock.

Figure 6:
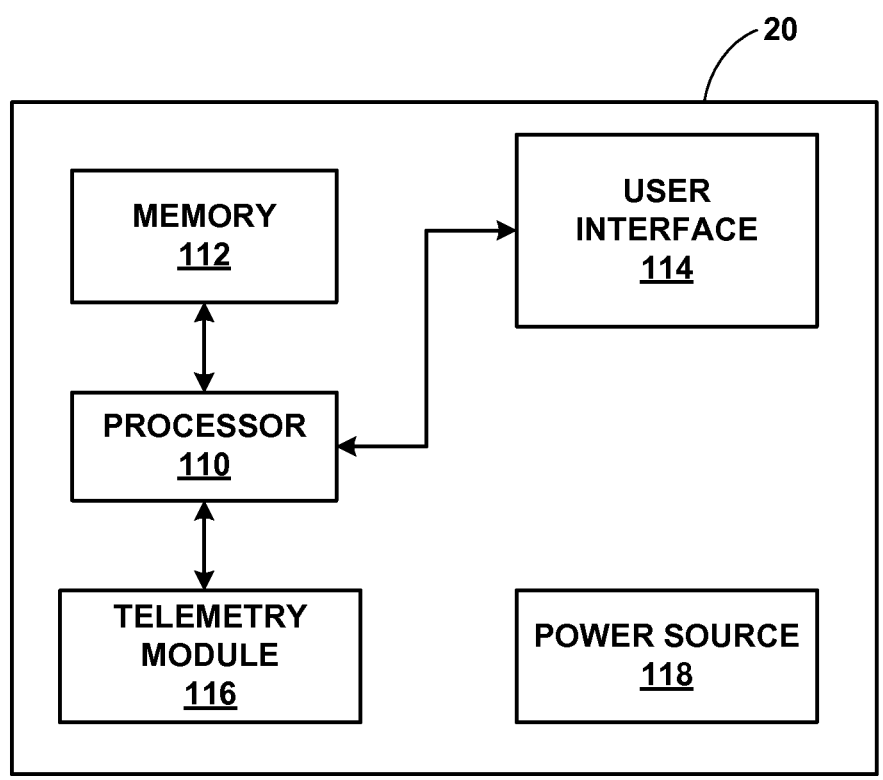
FIG. 6 is a functional block diagram illustrating an example configuration of the programmer of FIG. 1.

FIG. 6 is a functional block diagram illustrating an example configuration of external programmer 20 of FIG. 1. As shown in FIG. 6, programmer 20 may include a processor 110, memory 112, user interface 114, telemetry module 116, and power source 118. Programmer 20 may be a dedicated hardware device with dedicated software for programming of LPD 16 and/or SICD 30. Alternatively, programmer 20 may be an off-the-shelf computing device running an application that enables programmer 20 to program LPD 16 and/or SICD 30.

A user may use programmer 20 to configure the operational parameters of and retrieve data from LPD 16 and/or SICD 30 (FIG. 1). In one example, programmer 20 may communicate directly to both LPD 16 and SICD 30. In other examples, programmer may communicate to one of LPD 16 or SICD 30, and that device may relay any instructions or information to or from the other device. The clinician may interact with programmer 20 via user interface 114, which may include display to present graphical user interface to a user, and a keypad or another mechanism for receiving input from a user. In addition, the user may receive an alert or notification from SICD 30 indicating that a shock has been delivered, any other therapy has been delivered, or any problems or issues related to the treatment of patient 14.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 20 herein, and information used by processor 110 to provide the functionality ascribed to programmer 20 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before programmer 20 is used to program therapy for another patient.

Programmer 20 may communicate wirelessly with LPD 16 and/or SICD 30, such as using RF communication or proximal inductive interaction. This wireless communication is possible through the use of telemetry module 116, which may be coupled to an internal antenna or an external antenna. An external antenna that is coupled to programmer 20 may correspond to the programming head that may be placed over heart 12 or the location of the intend implant, as described above with reference to FIG. 1. Telemetry module 116 may be similar to telemetry modules 74 and 94 of respective FIGS. 4 and 5.

Telemetry module 116 may also be configured to communicate with another computing device via wireless communication techniques, or direct communication through a wired connection. Examples of local wireless communication techniques that may be employed to facilitate communication between programmer 20 and another computing device include RF communication according to the 802.11 or Bluetooth specification sets, infrared communication, e.g., according to the IrDA standard, or other standard or proprietary telemetry protocols. An additional computing device in communication with programmer 20 may be a networked device such as a server capable of processing information retrieved from LPD 16.

Figure 7:
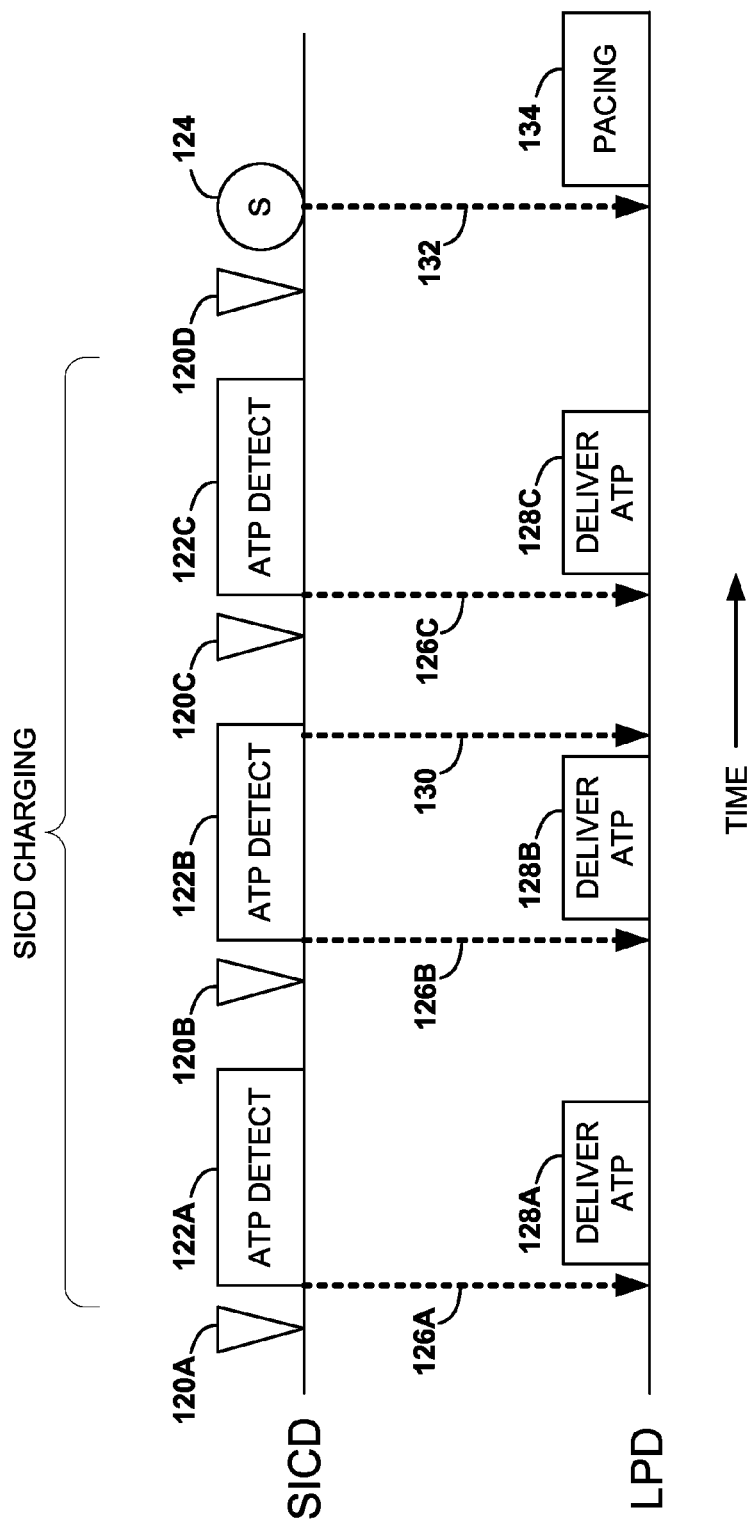
FIG. 7 is a timing diagram of an example technique for using one-way communication to instruct an LPD to deliver anti-tachycardia pacing (ATP).

FIG. 7 is a timing diagram of an example technique for using one-way communication from SICD 30 to instruct LPD 16 to deliver ATP. As shown in FIG. 7, SICD 30 and LPD 16 may perform certain actions and communicate with each other over time. The timelines for each of SICD 30 and LPD 16 are aligned vertically in time, as time increases to the right. In the one-way communication example of FIG. 7, SICD 30 may transmit communication messages and LPD 16 may receive the transmitted communication messages.

SICD 30 may be configured to monitor sensed electrical signals from heart 12 to detect tachyarrhythmias. At detection event 120A, SICD 30 may detect a tachyarrhythmia. In response to the detection of the tachyarrhythmia, SICD 30 may begin to charge in preparation for delivery an anti-tachyarrhythmia shock. Also, in response to detecting the tachyarrhythmia, SICD 30 may transmit a communication message 126A to LPD 16 that requests LPD 16 deliver ATP. LPD 16 may subsequently sense electrical signals from heart 12. If a tachyarrhythmia is detected by LPD 16, LPD 16 may begin delivery of ATP during ATP mode 128A. After SICD 30 transmits communication message 126A, SICD 30 may enter an ATP detection mode 122A configured to detect the ATP from LPD 16 and intrinsic electrical signals from heart 12.

While in ATP detection mode 122A, SICD 30 may be configured to determine that LPD 16 has determined to deliver ATP and has begun delivering ATP. Failure of LPD 16 to deliver ATP may indicate that LPD 16 did not detect a tachyarrhythmia. Since LPD 16 may not be configured to directly communicate with SICD 30, SICD 30 may monitor LPD 16 actions to infer reasons for certain actions or non-actions. In addition, or alternatively, ATP detection mode 122A may simply act as a filter to ATP signals to increase the sensitivity of SICD 30 to intrinsic signals during ATP. Alternatively, SICD 30 may implement a specific algorithm to discriminate between intrinsic beats and pacing pulses. If SICD 30 requests ATP to be delivered and determines that LPD 16 did not deliver ATP, SICD 30 may interpret the non-delivery as LPD 16 determining that a tachyarrhythmia has not been detected. In response to this determination, SICD 30 may adjust one or more tachyarrhythmia detection rules to reduce the detection sensitivity to tachyarrhythmias.

SICD 30 may continue to redetect tachyarrhythmia and request ATP from LPD 16 during the charging of SICD 30. ATP may be successful at terminating the tachyarrhythmia and/or allow time for SICD 30 to build up a sufficient charge for shock delivery. Therefore, SICD 30 may generate subsequent detection events 120B and 120C of a tachyarrhythmia and communication messages 126B and 126C requesting LPD 16 to deliver ATP during ATP modes 128B and 128C.

SICD 30 may provide additional communications to LPD 16. For example, during ATP detection mode 122B, SICD 30 may determine that the ATP delivered by LPD 16 has not captured or entrained the cardiac rhythm of heart 12. In other words, the ATP may have been ineffective at modulating the tachyarrhythmia of heart 12. SICD 30 may transmit communication message 130 instructing LPD 16 to adjust one or more parameter values of the parameters that define the ATP therapy. SICD 30 may suggest one or more parameter value adjustments or LPD 16 may independently determine one or more adjustments to parameter values. LPD 16 may then deliver subsequent ATP with the one or more updated parameter values.

Once SICD 30 completes charging for delivery of the shock, SICD 30 may detect the tachyarrhythmia one more time during detection event 120D. In response to detection of the tachyarrhythmia, SICD 30 may deliver shock 124. In response to delivery of shock 124, SICD may transmit communication message 132 to LPD 16 that indicates the shock was delivered. Alternatively, in response to detection of the tachyarrhythmia, SICD 30 may transmit a communication message to LPD 16 indicating that SICD 30 may deliver a shock imminently (e.g., the communication message may be transmitted 200 ms prior to delivery of the shock. LPD 16 may then enter a post-shock pacing mode 124 to deliver post-shock pacing if needed. LPD 16 may evaluate heart 12 for any arrhythmias (e.g., bradycardia or asystole) and enter the post-shock pacing mode 124 if post-shock pacing is deemed necessary. In some examples, LPD 16 may have enable shock detector 99 for detecting shock 124 and starting post-shock pacing. In other examples, LPD 16 may not be configured to deliver post-shock pacing.

Although the example of FIG. 7 includes three sessions of communication messages 126A-C and subsequent ATP sessions, other examples may include fewer or greater ATP sessions. For example, LPD 16 may only be able to deliver ATP once prior to SICD 30 completing charging and delivering a shock. In other examples, LPD 16 may deliver ATP four or more times.

In the one-way communication example of FIG. 7, SICD 30 may be configured to take various actions based on the detected, or undetected, pacing signals generated by LPD 16 and/or intrinsic electric signals sensed from heart 12. For example, if SICD 30 does not detect any ATP following a communication message requesting ATP (e.g., communication message 126A), SICD 30 may resend the request using a different communication vector (e.g., different set of electrodes or telemetry frequency) or higher power communication signal. In other examples, SICD 30 may send a message to LPD 16 indicating that entrainment of the cardiac rhythm occurred during ATP, but the tachyarrhythmia did not terminate. In this situation, LPD 16 may use the information to select different parameter values for the next session of ATP in an attempt to terminate the tachyarrhythmia without a shock. Alternatively, if the ATP entrained the cardiac rhythm, but the tachyarrhythmia did not terminate, SICD 30 may withhold an available shock and request that LPD 16 deliver ATP at least one more time to attempt to achieve tachyarrhythmia termination. In other examples, SICD 30 may transmit a communication message to LPD 16 indicating detection of a tachycardia even when LPD 16 does not detect a tachycardia. In this situation, LPD 16 may respond to SICD 30 by delivering a benign, non-ATP, train of pulses configured to signal SICD 30 that LPD 16 did not detect a tachycardia. In response to detecting the benign train of pulses, SICD 30 may adjust one or more arrhythmia detection rules or therapy parameters.

In other one-way communication examples, LPD 16 may be configured to transmit messages to SICD 30, and SICD 30 may be configured to receive such messages. For example, LPD 16 may be configured to monitor electrograms to detect tachyarrhythmias and instruct SICD 30 to "wake up" from a low power "sleep mode" to confirm the tachyarrhythmia and/ or deliver anti-tachyarrhythmia shock therapy.

In the example of FIG. 7, or any other examples in which ATP is delivered, LPD 16 and/or SICD 30 may be configured to monitor electrical and/or mechanical signals of heart 12 to determine if the tachyarrhythmia has been terminated by delivery of the ATP. In response to determining that the tachyarrhythmia has been terminated by the ATP, LPD 16 and/or SICD 30 may cancel the delivery of any additional ATP and/or anti-tachyarrhythmia shock therapy because the tachyarrhythmia is no longer present.

Figure 8:
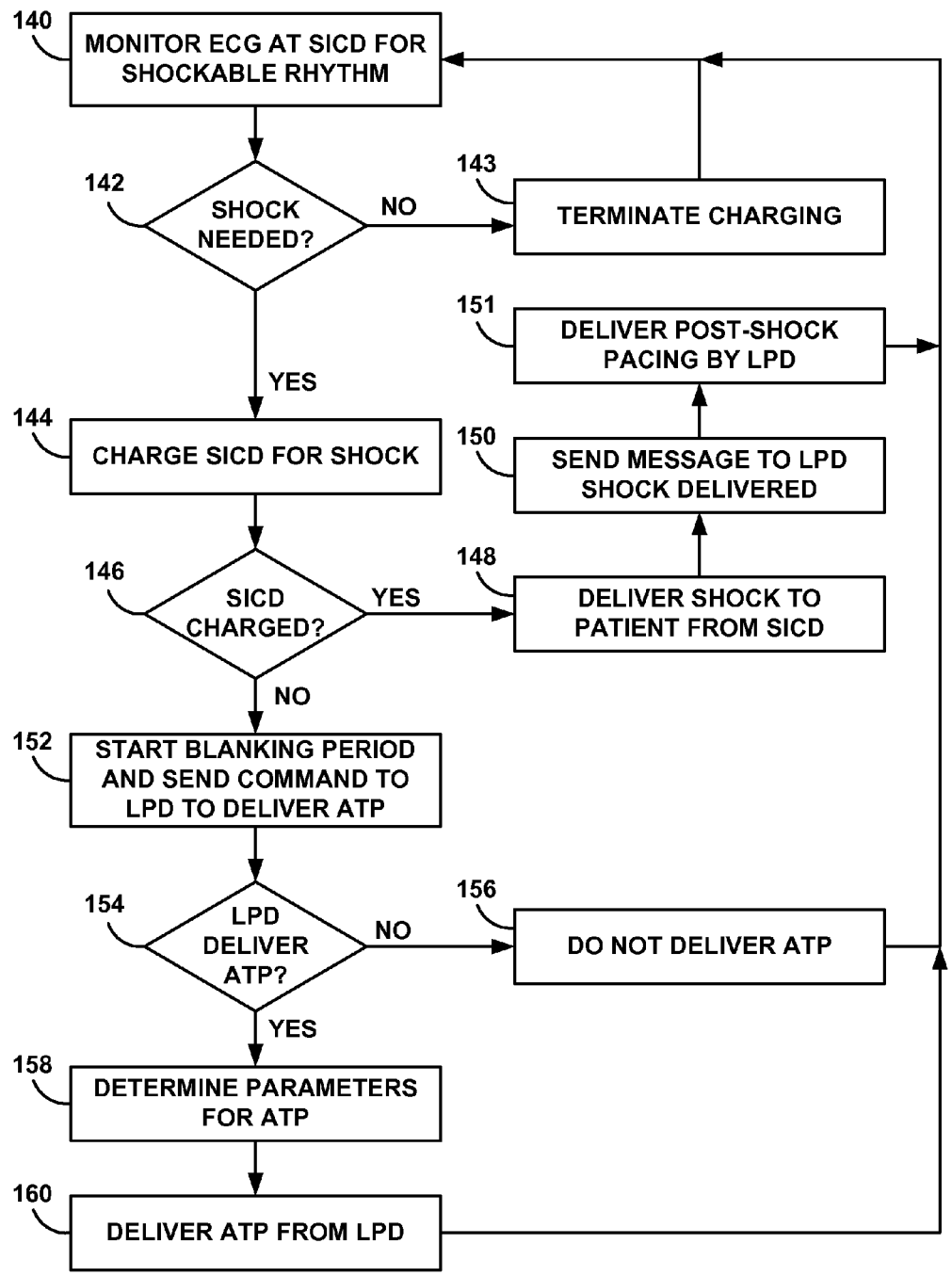
FIG. 8 is a flow diagram of an example technique for using one-way communication to instruct an LPD to deliver anti-tachycardia pacing (ATP).

FIG. 8 is flow diagram of an example technique for using one-way communication to instruct LPD 16 to deliver anti-tachycardia pacing (ATP). The example process of FIG. 8 is described with respect to SICD 30 and LPD 16 may relate to the timing diagram of FIG. 7. In addition, the process of FIG. 8 may be implemented using two or more LPDs. In other examples, the one-way communication may be switched between SICD 30 and LPD 16 (i.e., LPD 16 may be configured to transmit communication messages to SICD 30 or SICD 30 may be configured to transmit communication messages to LPD 16).

As shown in FIG. 8, processor 70 of SICD 30 monitors a sensed ECG for a shockable rhythm (140). For example, processor 70 may detect tachyarrhythmias as a shockable rhythm eligible for anti-tachycardia therapy. If processor 70 determines that no shock is needed ("NO" branch of block 142), processor 70 may continue to monitor the ECG for tachyarrhythmias (140). If SICD 30 has already started to charge for an impending shock, processor 70 may terminate the charging sequence (143) before continuing to monitor the ECG (140). This termination of charging may occur if the ATP terminated the tachyarrhythmia or the tachyarrhythmia becomes otherwise non-shockable. If processor 70 determines that a shock is needed to treat a detected arrhythmia ("YES" branch of block 142), processor 70 may begin charging shock module 75 of SICD 30 (144). In other examples, processor 70 may delay beginning charging until after ATP is determined to be unsuccessful to save energy in the situation in which ATP terminates the arrhythmia. If SICD 30 is charged ("YES" branch of block 146), processor 70 may command signal generator 76 to deliver an anti-tachyarrhythmia shock to patient 14 (148). Processor 70 may then send a communication message to LPD 16 to indicate that a shock has been delivered (150). In response to receiving the communication message, processor 90 of LPD 16 may deliver post-shock pacing to heart 14 (151) before processor 70 again monitors heart 12 for tachyarrhythmias (140).

If processor 70 determines that SICD 30 is not charged and ready to deliver a shock ("NO" branch of block 146), processor 70 may start a blanking period and send a communication message, or command, to LPD 16 to deliver ATP (152). The blanking mode may prevent further detection of tachyarrhythmia during ATP. In addition to the blanking period, processor 70 may enter an ATP detection mode that monitors the ATP and intrinsic signals to determine if the ATP is effective at capturing the rhythm of heart 12. If the ATP is not effective, processor 70 may transmit a message to LPD 16 requesting a change to one or more parameter values that defines the ATP to improve the ATP therapy. In some examples, SICD 30 may transmit ECG data and/or suggested parameter adjustments to LPD 16 such that LPD 16 may adjust one or more parameter values for ATP based on the ECG data obtained by SICD 30 instead.

Processor 90 of LPD 16 may then sense electrical signals from heart 12 and determine if ATP should be delivered (154). For example, processor 90 may determine if a tachyarrhythmia is detected and/or if LPD 16 is operational for ATP delivery. If processor 90 determines that ATP should not be delivered ("NO" branch of block 154), processor 90 may determine that ATP is not to be delivered and processor 70 of SICD 30 may continue to monitor heart 12 for shockable rhythms (140). If processor 90 determines that ATP should be delivered ("YES" branch of block 154), processor 90 may determine the parameter values for ATP (158) and deliver ATP to heart 12 (160). Processor 90 may determine the parameter values from instructions stored in memory 92 and/ or based on the sensed tachyarrhythmia signal from heart 12. In this manner, ATP may be tailored to the specific conditions of the tachyarrhythmia, such as pulse width, pulse rate, amplitude, and ATP duration. In other examples, the parameter values that define ATP may merely be retrieved from memory 92 prior to delivering ATP. Then, after delivering ATP, any changes to the parameter values that define subsequent ATP may be made based on instructions in memory 92, the sensed tachyarrhythmia signal and/or instructions from SICD 30. SICD 30 or LPD 16 may determine one or more of the parameter values that at least partially define the subsequent ATP based on the sensed signals.

After delivery of ATP, processor 70 may again monitor ECGs for tachyarrhythmias. For example, processor 70 may determine if the ATP was successful at converting heart 12 to a sinus rhythm during charging of the SICD 30. If ATP was successful, processor 70 may terminate charging and abort or overturn the previous determination to deliver an anti-tachyarrhythmia shock.

Figure 9:
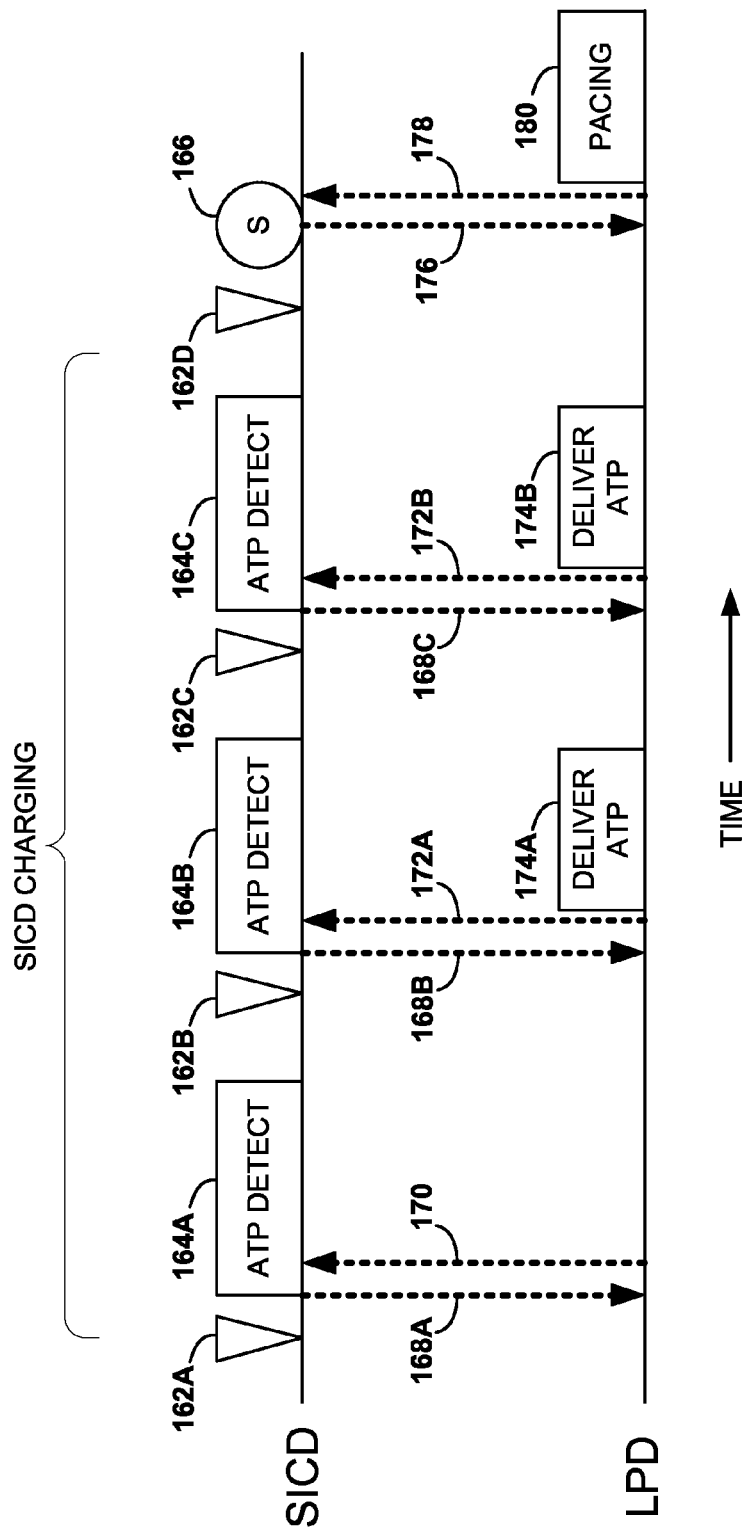
FIG. 9 is a timing diagram of an example process for using two-way communication to confirm tachyarrhythmia first detected by the SICD.

FIG. 9 is a timing diagram of an example process for using two-way communication to confirm tachyarrhythmia first detected by SICD 30. The example of FIG. 9 may be similar to the example of FIG. 7. However, the example process of FIG. 9 also implements two-way communication between SICD 30 and LPD 16. The timelines for each of SICD 30 and LPD 16 are aligned vertically in time, as time increases to the right. In the two-way communication example of FIG. 9, both SICD 30 and LPD 16 may transmit and receive communication messages.

SICD 30 may be configured to monitor sensed electrical signals from heart 12, such as detection of tachyarrhythmias. At detection event 162A, SICD 30 may detect a tachyarrhythmia. In response to the detection of the tachyarrhythmia, SICD 30 may begin to charge in preparation for delivery an anti-tachyarrhythmia shock. SICD 30 may also, in response to detecting the tachyarrhythmia, begin ATP detection mode 164A and transmit a communication message 168A to LPD 16 that requests LPD 16 deliver ATP. LPD 16 may subsequently sense electrical signals from heart 12. If a tachyarrhythmia is detected by LPD 16, LPD 16 may begin delivery of ATP. However, in the example of FIG. 9, LPD 16 may not detect the tachyarrhythmia and transmit a communication message 170 to SICD 30 indicating a rejection of the tachyarrhythmia determination. Since LPD 16 did not detect an arrhthmia, LPD 16 also may not deliver ATP. In some examples, communication message 170 may not confirm the SICD detection of the tachyarrhythmia or indicate that ATP will not be delivered for another reason (e.g., improper electrode capture or low LPD battery charge). ATP detection mode 164 may be similar to ATP detection mode 122 of FIG. 7.

In other examples, SICD 30 and/or LPD 16 may transmit detected data (e.g., ECG information, morphology, detected R-R intervals, etc.) in response to two or more consecutive conflicting detections and non-detections of a tachyarrhythmia. The device receiving the detected data may adjust one or more detection rules or parameters based on the data to resolve the discrepancy between devices.

SICD 30 may continue to redetect tachyarrhythmia and request ATP from LPD 16 during the charging of SICD 30. ATP may be successful at terminating the tachyarrhythmia and/or allow time for SICD 30 to build up a sufficient charge for shock delivery. Therefore, SICD 30 may generate subsequent detection events 162B and 162C of a tachyarrhythmia and communication messages 168B and 168C requesting LPD 16 to deliver ATP. However, in response to receiving communication message 168B, LPD 16 may detect the tachyarrhythmia and transmit a communication message 172A confirming the detection of the tachyarrhythmia. In addition, LPD 16 may deliver ATP during ATP mode 174A. LPD 16 may also deliver ATP during ATP mode 174B in response to receiving communication message 168B requesting ATP delivery. In other examples, SICD 30 and LPD 16 may perform additional handshaking communication when the tachyarrhythmia is confirmed by LPD 16. For example, communication messages 168 may request confirmation of the tachyarrhythmia, and in response to receiving affirmative confirmation from confirmation messages 172, SICD 30 may transmit an additional communication message or command for LPD 16 to deliver ATP.

Similar to the example of FIG. 7, SICD 30 may provide additional communications to LPD 16. For example, during ATP detection modes 164, SICD 30 may determine that the ATP delivered by LPD 16 is not capturing or entraining the cardiac rhythm of heart 12. In other words, the ATP may be ineffective at modulating the tachyarrhythmia of heart 12. SICD 30 may transmit communication messages instructing LPD 16 to adjust one or more parameter values of the parameters that define the ATP therapy.

Once SICD 30 completes charging for delivery of the shock, SICD 30 may detect the tachyarrhythmia one more time during detection event 162D. In response to detection of the tachyarrhythmia, SICD 30 may deliver shock 166. In response to delivery of shock 166, SICD may transmit communication message 176 to LPD 16 that indicates the shock was delivered. LPD 16 may then respond with communication message 178 confirming the shock was delivered and indicating that post-shock pacing may be delivered. LPD 16 may subsequently enter a post-shock pacing mode 180 to deliver post-shock pacing. In some examples, LPD 16 may have enabled shock detector 99 for detecting shock 166 and starting post-shock pacing. In other examples, LPD 16 may not be configured to deliver post-shock pacing.

SICD 30 continued to charge for a shock even after LPD 16 did not confirm the tachyarrhythmia with communication message 170. SICD 30 may continue charging until SICD 30 receives a predetermined number of consecutive rejections from LPD 16 (e.g., two or three rejections) and/or SICD 30 no longer detects the tachyarrhythmia. In other examples, SICD 30 may terminate charging and preparation for a shock in response to receiving the rejection message 170 from LPD 16.

Although the example of FIG. 9 includes three sessions of communication messages and subsequent ATP sessions, other examples may include fewer or greater ATP sessions. For example, LPD 16 may only able to deliver ATP once prior to SICD 30 completing charging and delivering a shock. In other examples, LPD 16 may deliver ATP four or more times.

In the two-way communication example of FIG. 9, SICD 30 may be configured to request information from LPD 16 on why ATP was not delivered. For example, such a request may be sent by SICD 30 in response to receiving the rejection message 170. LPD 16 may responsively transmit a message indicating one or more reasons why ATP was not delivered. These reasons may indicate which aspects of LPD 16 are functioning properly (e.g., sufficient battery charge, sufficient electrode contacts, and functioning electronics) such that ATP non-delivery is due to appropriate sensing of the patient condition. Alternatively, LPD 16 may transmit, with the rejection message 170, a reason for why the rejection message was generated. If ATP was not delivered due to no detection of a tachyarrhythmia, SICD 30 may transmit new detection criteria to LPD 16. In other examples, SICD 30 may transmit new ATP parameter values if the failure to deliver ATP was due to a hardware issue with LPD 16. In some example, SICD 30 may even attempt to provide effective ATP if LPD 16 is otherwise unable to provide ATP to heart 12. If LPD 16 determines that SICD 30 has not provided communication or has received information indicating that SICD 30 is no longer functioning properly, LPD 16 may be configured to disable communication with SICD 30.

In some examples, LPD 16 may respond to SICD 30 indicating that ATP will not be delivered and requesting that SICD 30 deliver a shock as fast as possible. For example, LPD 16 may determine that the tachyarrhythmia is too fast to be terminated with ATP or activity sensor 100 may indicate that heart 12 is in asystole. Other confirmation rules may also cause LPD 16 to skip deliver of ATP.

In situations in which there is disagreement between SICD 30 and LPD 16 about whether or not patient 14 is experiencing a tachyarrhythmia (e.g., one device detects the tachyarrhythmia and another device does not), one of the devices may be configured to override the other device. For example, if SICD 30 detects a tachyarrhythmia requiring a shock therapy and LPD 16 does not detect the tachyarrhythmia, SICD 30 may override LPD 16 and deliver the shock. This override may be implemented to ensure that a potential tachyarrhythmia is treated. Similarly, detection of a tachyarrhythmia by LPD 16 and no detection of the tachyarrhythmia by SICD 30, may result in SICD 30 delivering shock therapy to ensure that patient 14 is treated. In other examples, additional information such as data or detected waveforms may be communicated between the devices such that a device can analyze the data and determine whether or not a tachyarrhythmia is present before delivering a shock.

Figure 10A:
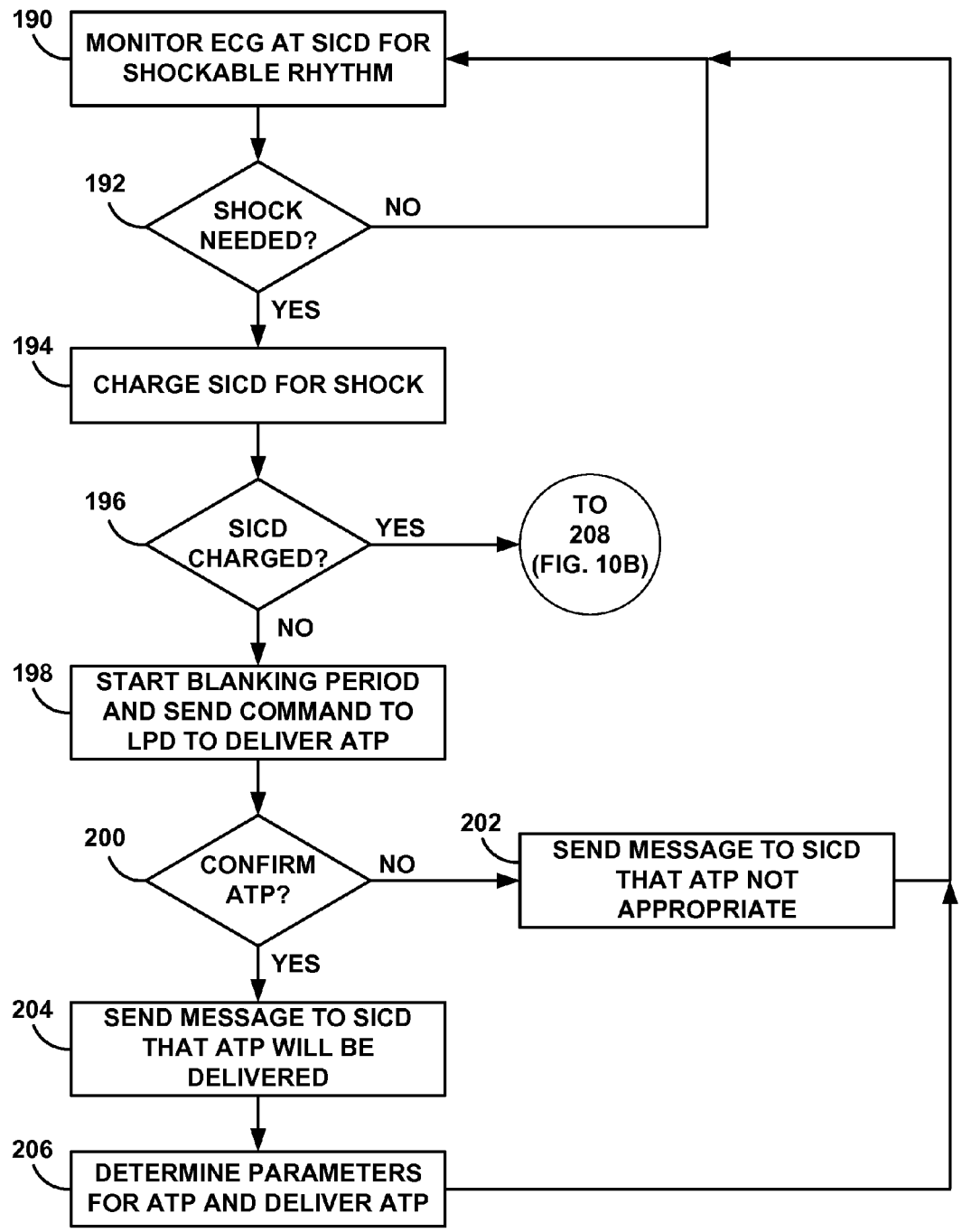
FIGS. 10A and 10B are flow diagrams of an example process for using two-way communication to confirm tachyarrhythmia first detected by the SICD.
Figure 10B:
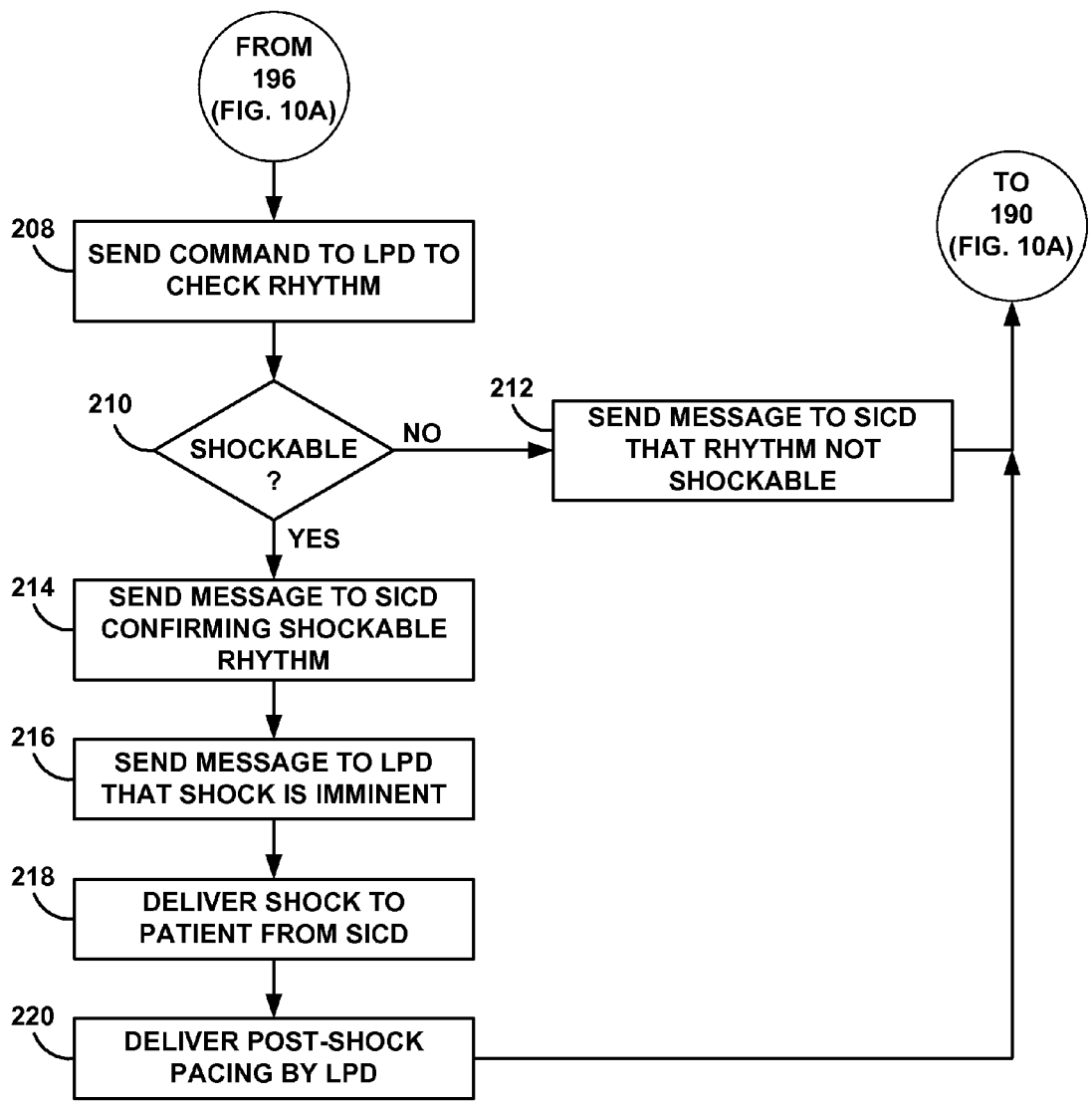

FIGS. 10A and 10B are flow diagrams of an example process for using two-way communication to confirm tachyarrhythmia first detected by SICD 30. The example process of FIGS. 10A and 10B is described with respect to SICD 30 and LPD 16 may relate to the timing diagram of FIG. 9. In addition, the process of FIGS. 10A and 10B may be implemented using two or more LPDs.

As shown in FIGS. 10A and 10B, processor 70 of SICD 30 monitors a sensed ECG for a shockable rhythm (190). For example, processor 70 may detect tachyarrhythmias as a shockable rhythm eligible for anti-tachycardia therapy. If processor 70 determines that no shock is needed ("NO" branch of block 192), processor 70 may continue to monitor the ECG for tachyarrhythmias (190). If SICD 30 has already started to charge for an impending shock, processor 70 may terminate the charging sequence before continuing to monitor the ECG (190). This termination of charging may occur if the ATP terminated the tachyarrhythmia or the tachyarrhythmia becomes otherwise non-shockable. If processor 70 determines that a shock is needed to treat a detected arrhythmia ("YES" branch of block 192), processor 70 may begin charging shock module 75 of SICD 30 (194). If SICD 30 is charged ("YES" branch of block 196), processor 70 may transmit a command or message to LPD 16 to check for any detectable tachyarrhythmias (208). If processor 90 of LPD 16 does not detect a shockable rhythm ("NO" branch of block 210), processor 90 transmits a message to SICD 30 indicating that the detected rhythm was not shockable (212). Processor 70 may then proceed to monitor for any tachyarrhythmias (190).

If processor 90 of LPD 16 determines that a shockable tachyarrhythmia was detected ("YES" branch of block 210), processor 90 may send a message to SICD 30 confirming that a shockable rhythm (e.g., a tachycardia eligible for shock) was detected (214). In response to the confirmation, processor 70 may send a message to LPD 16 that a shock is imminent (216). This message of an imminent shock may allow LPD 16 to enter a shock detection mode. Processor 70 may then deliver the shock from SICD 30 (218). In response to detecting that the shock was delivered, processor 90 may deliver post-shock pacing to heart 12 (220) prior to further monitoring of ECGs by SICD 30 (190). In other examples in which LPD 16 is not configured to detect the shock, processor 70 of SICD 30 may send a message to LPD 16 indicating that the shock has been delivered so that LPD 16 can begin post-shock pacing if needed.

If processor 70 determines that SICD 30 is not charged and ready to deliver a shock ("NO" branch of block 196), processor 70 may start a blanking period and send a communication message, or command, to LPD 16 to deliver ATP (198). The blanking mode may prevent further detection of tachyarrhythmia during ATP. In addition to the blanking period, processor 70 may enter an ATP detection mode that monitors the ATP and intrinsic signals to determine if the ATP is effective at capturing the rhythm of heart 12. If the ATP is not effective, processor 70 may transmit a message to LPD 16 requesting a change to one or more parameter values that defines the ATP to improve the ATP therapy.

Processor 90 of LPD 16 may then sense electrical signals from heart 12 and determine if ATP should be delivered (200). For example, processor 90 may determine if a tachyarrhythmia is detected and/or if LPD 16 is operational for ATP delivery. If processor 90 determines that ATP should not be delivered ("NO" branch of block 200), processor 90 may send a communication message to SICD 30 that ATP is not appropriate or that a tachyarrhythmia is not detected (202). SICD 30 may then continue to monitor heart 12 for shockable rhythms (190). If processor 90 determines that ATP should be delivered ("YES" branch of block 200), processor 90 may send a communication message to SICD 30 confirming that ATP will be delivered (204). Processor 90 may then determine the parameter values for ATP and deliver ATP to heart 12 (206). Processor 90 may determine the parameter values from instructions stored in memory 92 and/or based on the sensed tachyarrhythmia signal from heart 12. In this manner, ATP may be tailored to the specific conditions of the tachyarrhythmia, such as pulse width, pulse rate, amplitude, and ATP duration. In other examples, the parameter values that define ATP may merely be retrieved from memory 92 prior to delivering ATP. Then, after delivering ATP, any changes to the parameter values that define subsequent ATP may be made based on instructions in memory 92, the sensed tachyarrhythmia signal and/or instructions from SICD 30. SICD 30 or LPD 16 may determine one or more of the parameter values that at least partially define the subsequent ATP based on the sensed signals.

After delivery of ATP, processor 70 may again monitor ECGs for tachyarrhythmias. For example, processor 70 may determine if the ATP was successful at returning heart 12 to a sinus rhythm during charging of the SICD 30. If ATP was successful, processor 70 may terminate charging and abort or overturn the previous determination to deliver an anti-tachyarrhythmia shock.

Figure 11:
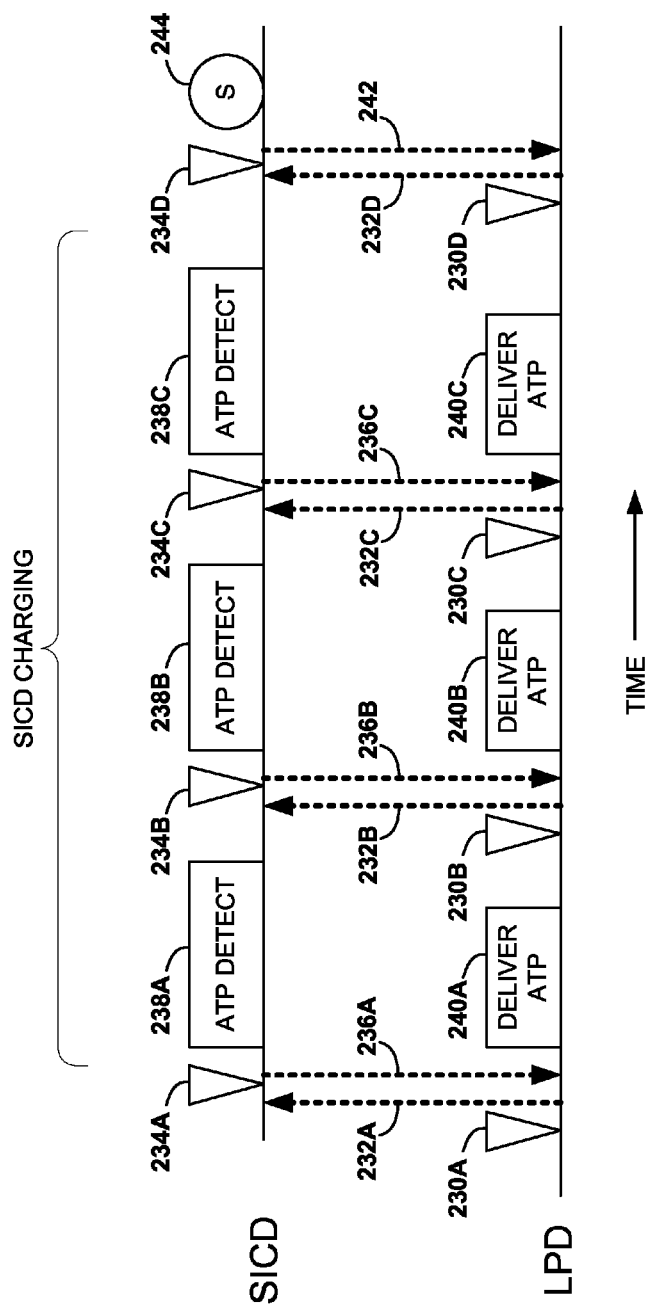
FIG. 11 is a timing diagram of an example process for using two-way communication to confirm tachyarrhythmia first detected by the LPD.

FIG. 11 is a timing diagram of an example process for using two-way communication to confirm tachyarrhythmia first detected by LPD 16. The example of FIG. 11 may be similar to the example of FIG. 9. However, the example process of FIG. 11 uses two-way communication between SICD 30 and LPD 16 to confirm the detection of a tachyarrhythmia by LPD 16. The timelines for each of SICD 30 and LPD 16 are aligned vertically in time, as time increases to the right. In the two-way communication example of FIG. 11, both SICD 30 and LPD 16 may transmit and receive communication messages.

LPD 16 may be configured to monitor sensed electrical signals from heart 12, such as tachyarrhythmias that may be treated with anti-tachycardia pacing and/or shocks. At detection event 230A, LPD 16 may detect a tachyarrhythmia. In response to the detection of the tachyarrhythmia, LPD 16 may transmit a communication message 232A to SICD 30 to confirm the detection of the tachyarrhythmia. In some examples, SICD 30 may be in a low power "sleep mode" when communication message 232A is received. In response to receiving this message, SICD 30 may exit the sleep mode and become active. The sleep mode may be a power saving mode to conserve batter power.

At detection event 234A, SICD 30 may detect the tachyarrhythmia. In response to the detection of the tachyarrhythmia, SICD 30 may begin to charge in preparation for delivery an anti-tachyarrhythmia shock. SICD 30 may also, in response to detecting the tachyarrhythmia, begin ATP detection mode 238A and transmit a communication message 236A to LPD 16 that confirms the detection of the tachyarrhythmia. In response to receiving communication message 236A, LPD 16 may begin delivering ATP during ATP mode 240A.

This process of initial detection of the tachyarrhythmia at detection events 230B, 230C, and 230D may continue until SICD 30 charging is complete or the tachyarrhythmia terminates. During charging, LPD 16 may transmit communication messages 232B and 232C and deliver ATP during ATP modes 240B and 240C. In addition, SICD 30 may also detect the tachyarrhythmia at detection events 234B and 234C, enter into ATP detection modes 238B and 238C, and transmit communication messages 236B and 236C confirming the respective tachyarrhythmia detection.

In response to re-detecting the tachyarrhythmia at detection event 230D, LPD 16 may again transmit communication message 232D requesting confirmation of the tachyarrhythmia. However, SICD 30 also detects that charging has been completed. In response to continued detection of the tachyarrhythmia at detection event 234D, SICD 30 may transmit a communication message 242 informing LPD 16 that a shock will be delivered and deliver shock 244.

In other examples, SICD 30 may transmit communication message 242 after shock 244 is delivered or not transmit message 242 since LPD 16 may have a shock detector enabled to detect the delivery of shock 244. In some examples, LPD 16 may deliver post-shock pacing after shock 244 is delivered. The process of FIG. 11 may be completed with fewer or greater than three sessions of ATP. The duration of the process in FIG. 11 may be dependent upon the amount of time needed to charge SICD 30 and the predetermined durations of each ATP mode 240.

Figure 12:
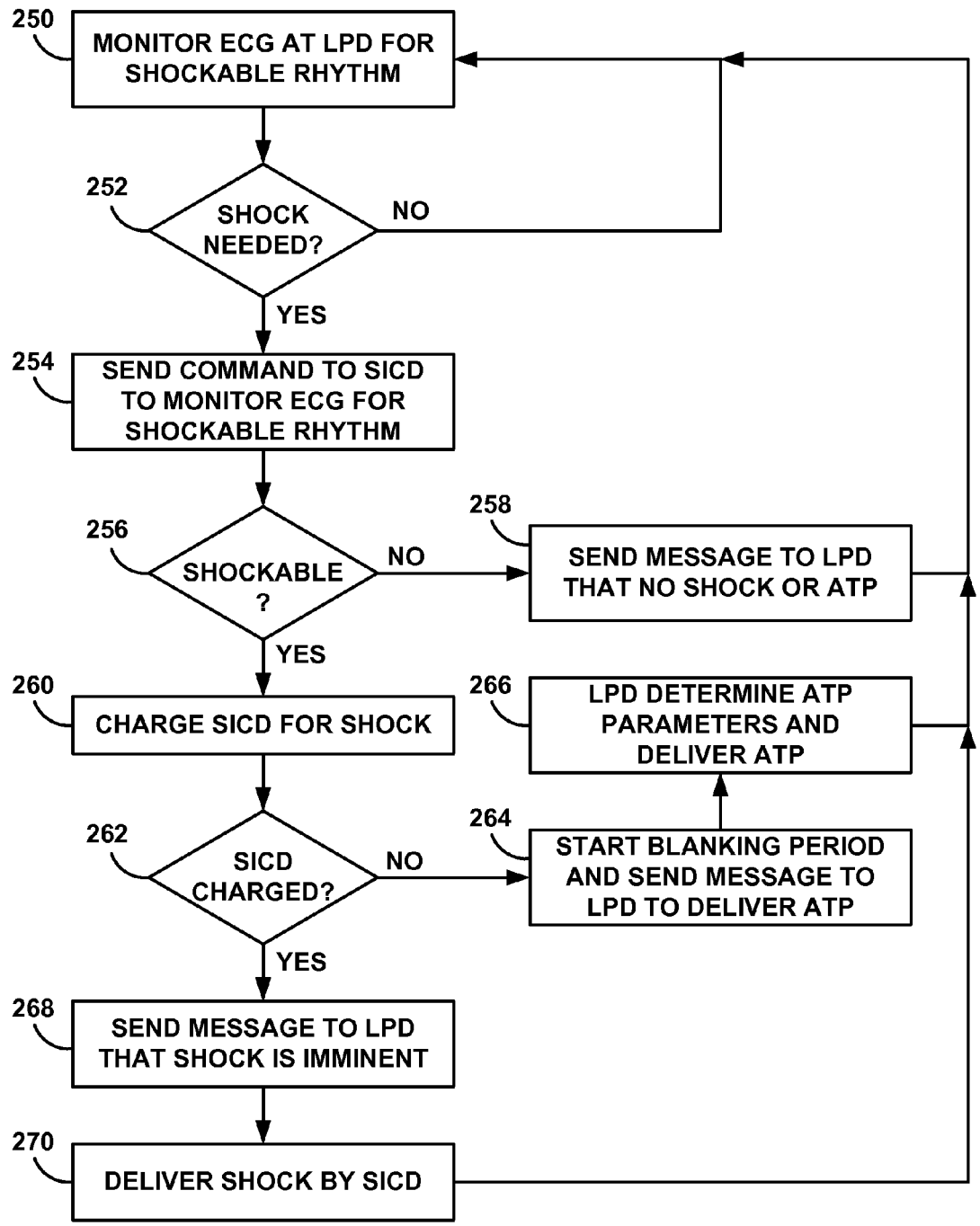
FIG. 12 is a flow diagram of an example process for using two-way communication to confirm tachyarrhythmia first detected by the LPD.

FIG. 12 is a flow diagram of an example process for using two-way communication to confirm tachyarrhythmia first detected by LPD 16. The example process of FIG. 12 is described with respect to SICD 30 and LPD 16 may relate to the timing diagram of FIG. 11. In addition, the process of FIG. 12 may be implemented using two or more LPDs.

As shown in FIG. 12, processor 90 of LPD 16 monitors a sensed EGM for a shockable rhythm (250). For example, processor 90 may detect tachyarrhythmias as a shockable rhythm eligible for anti-tachycardia therapy. If processor 90 determines that no shock is needed ("NO" branch of block 252), processor 90 may continue to monitor the EGM for tachyarrhythmias (250). If SICD 30 has already started to charge for an impending shock prior to determining that the shock is no longer needed, processor 90 may communicate to SICD 30 to terminate the charging sequence. This termination of charging may occur if the ATP terminated the tachyarrhythmia or the tachyarrhythmia becomes otherwise nonshockable. If processor 90 determines that a shock is needed to treat a detected arrhythmia ("YES" branch of block 252), processor 90 sends a communication message to SICD 30 to monitor the ECG for the shockable tachyarrhythmia rhythm (254).

If processor 70 of SICD 30 does not detect the tachyarrhythmia ("NO" branch of block 256), processor 70 transmits a communication message to LPD 16 indicating that no shock or ATP should be delivered to patient 14 (258). Processor 90 may continue to monitor heart for tachyarrhythmias (250). If, however, processor 70 detects the tachyarrhythmia requiring therapy ("YES" branch of block 256), processor 70 may begin charging shock module 75 of SICD 30 (260). If SICD 30 is charged ("YES" branch of block 262), processor 70 may send a message to LPD 16 that a shock is imminent (268). This message of an imminent shock may allow LPD 16 to enter a shock detection mode. Processor 70 may then deliver the shock to patient 14 (270). After the shock is delivered, processor 90 may continue to monitor heart 12 for tachyarrhythmias (250). In other examples in which LPD 16 is not configured to detect the shock, processor 70 of SICD 30 may send a message to LPD 16 indicating that the shock has been delivered so that LPD 16 can begin post-shock pacing if needed.

If processor 70 determines that SICD 30 is not charged and ready to deliver a shock ("NO" branch of block 262), processor 70 may start a blanking period and send a communication message, or command, to LPD 16 to deliver ATP (264). The blanking mode may prevent further detection of tachyarrhythmia during ATP. In addition to the blanking period, processor 70 may enter an ATP detection mode that monitors the ATP and intrinsic signals to determine if the ATP is effective at capturing the rhythm of heart 12. If the ATP is not effective, processor 70 may transmit a message to LPD 16 requesting a change to one or more parameter values that defines the ATP to improve the ATP therapy.

Processor 90 of LPD 16 may then determine the parameter values to define the ATP and deliver the ATP to heart 12 (266). Processor 90 may then continue to monitor heart 12 for tachyarrhythmias (250). This process of FIG. 12 may continue until SICD 30 is fully charged and a shock is delivered or the tachyarrhythmia is no longer detected. In other examples, the parameter values that define ATP may merely be retrieved from memory 92 prior to delivering ATP. Then, after delivering ATP, any changes to the parameter values that define subsequent ATP may be made based on instructions in memory 92, the sensed tachyarrhythmia signal and/or instructions from SICD 30. SICD 30 or LPD 16 may determine one or more of the parameter values that at least partially define the subsequent ATP based on the sensed signals.

In the examples of FIGS. 7-12, multiple LPDs may be used to detect tachyarrhythmias and/or deliver ATP. In some examples, the ATP may be coordinated between LPDs implanted in different chambers of the heart. In these examples, tachyarrhythmia confirmation may be received from each of the LPDs and SICD 30 or only one of the other devices within the system. For example, if an LPD implanted within right atrium 22 detects a tachyarrhythmia, only confirmation from SICD 30 or an LPD implanted within a different chamber of heart 12 may be needed to proceed with delivery of ATP and/or shock therapy.

Although the examples of FIGS. 7-12 generally describe charging of SICD 30 during ATP delivery by LPD 16, charging of SICD 30 may occur after ATP delivery in other examples. For example, SICD 30 may wait for LPD 16 to deliver one or more sessions of ATP before beginning to charge for delivery of anti-tachyarrhythmia shock therapy. In this manner, SICD 30 may not need to charge the shock module in situations in which ATP is effective at terminating the tachyarrhythmia. SICD 30 may begin charging after SICD 30 determines that the tachyarrhythmia continues after one or more sessions of ATP or after LPD 16 requests SICD 30 begin charging due to ineffective ATP. In some examples, SICD 30 may determine if charging the shock module occurs during ATP delivery of after confirmation that ATP was unsuccessful. For example, SICD 30 may begin charging prior to, or concurrent with, ATP delivery to treat very fast tachyarrhythmia or other severe conditions that cannot wait for ATP effectiveness to be assessed.

In some situations, SICD 30 and LPD 16 may generate conflicting or disagreeing commands with regard to the detection or non-detection of tachyarrhythmias and/or suggested therapies (e.g., anti-tachyarrhythmia shock therapy or ATP). Alternatively, communication could fail between SICD 30 and LPD 16. In any situation, SICD 30 or LPD 16 may revert to a master device that overrules the slave device. For example, SICD 30 may default to the master device that determines which actions to take. In other examples, LPD 16 may default to the master device. In this manner, the system of SICD 30 and LPD 16 may be configured to resolve any detection or therapeutic discrepancies.

Although SICD 30 and LPD 16 may deliver therapy in a coordinated manner using one-way or two-way communication, the coordinated delivery of therapy may alternatively occur even without direct communication in other examples. For example, SICD 30 and LPD 16 may function according to respective algorithms. However, one or both of the devices may monitor the activities of the other device. In this manner, patient 14 may benefit from coordinated therapy without the devices needing to communicate with each other or the additional power consumption associated with communication protocols.

In one example, SICD 30 may operate with a tachyarrhythmia detection algorithm and LPD 16 may operate with its own tachyarrhythmia detection algorithm. In response to detecting a shockable tachyarrhythmia, SICD 30 may begin to charge and monitor for any ATP delivered by LPD 16. Separately, LPD 16 may deliver ATP in response to detecting tachycardia that may be treated by ATP and/or monitor for any shocks delivered by SICD 30. In response to detecting that ATP was delivered by LPD 16, SICD 30 may confirm that LDP 16 detected the tachyarrhythmia and adjust future detection rules and/or subsequent delivery of anti-tachyarrhythmia shock therapy accordingly. In response to detecting a shock, LPD 16 may terminate ATP (e.g., immediately upon detecting the shock) and begin delivery of post-shock therapy as described herein, in some examples.

Figure 13:
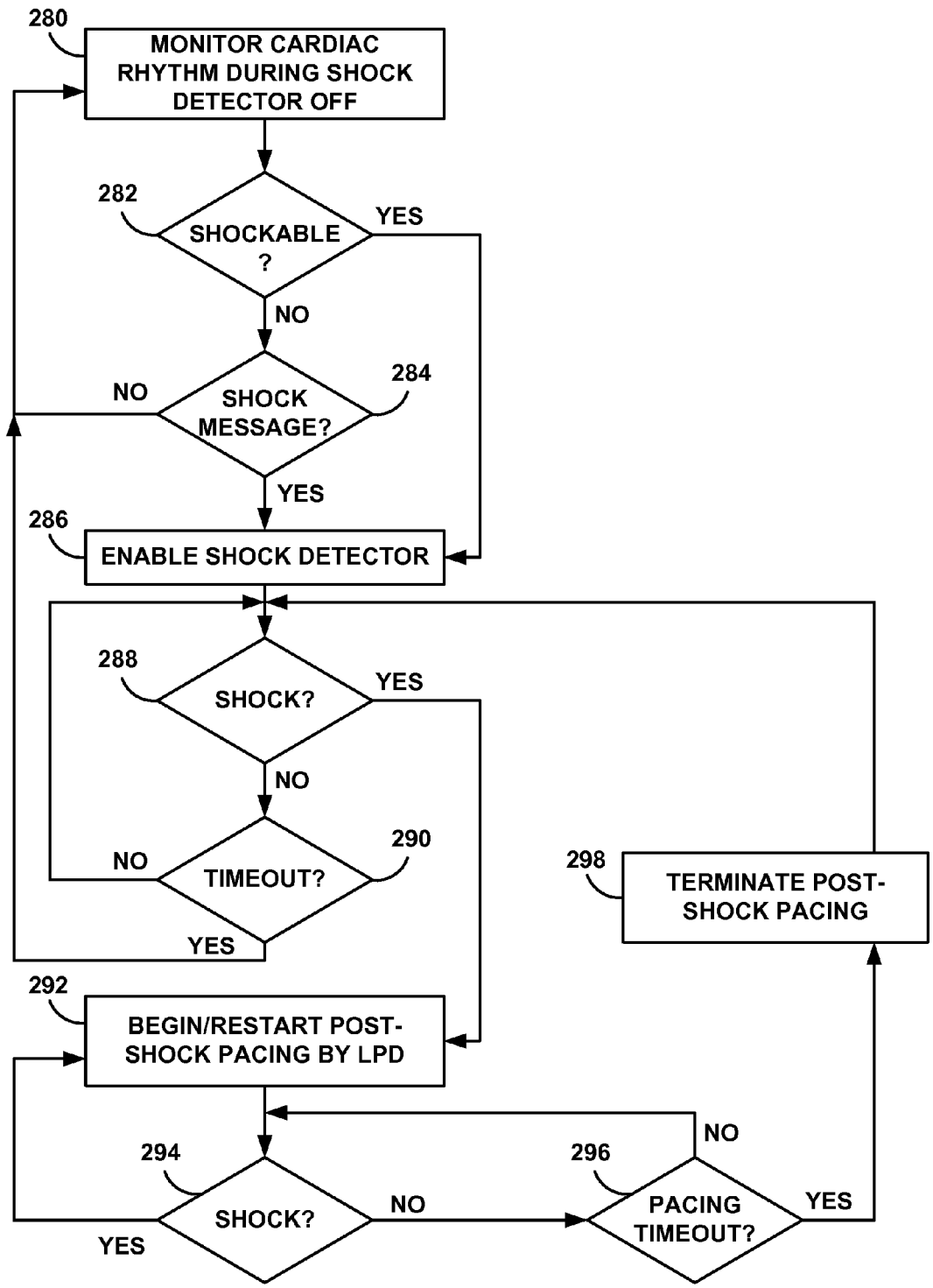
FIG. 13 is a flow diagram of an example process for delivering post-shock therapy by an LPD.

FIG. 13 is a flow diagram of an example process for delivering post-shock therapy by LPD 16. The example of FIG. 13 will be described with respect to LPD 16 operating without direct communication to SICD 30 or with direct communication to SICD 30. However, LPD 16 may operate under only one of these conditions in some examples. In this manner, LPD 16 may be capable of determining when to deliver post-shock pacing with or without any instruction from another device.

As shown in FIG. 13, processor 90 of LPD 16 may monitor a cardiac rhythm from an electrical signal sensed from heart 12 (280). This monitoring may occur during a period of time when shock detector 99 is off or disabled. Disabling of shock detector 99 may reduce power consumption by LPD 16 and extend the battery life of power source 102. Therefore, processor 90 may need to enable shock detector 99 at some point during operation of LPD 16.

If processor 90 detects a shockable tachyarrhythmia (e.g., an arrhythmia eligible for anti-tachyarrhythmia shock therapy) ("YES" branch of block 282), processor 90 proceeds to enable shock detector 99 (286). If processor 90 has not detected a shockable tachyarrhythmia ("NO" branch of block 282), processor 90 may check to determine if any message regarding a tachyarrhythmia or shock as been received from a different device such as SICD 30 (284). For example, processor 90 may conduct periodic radio polling to search for communications from SICD 30 indicating that shock detector 99 should be enabled. If no message regarding a shock has been received ("NO" branch of block 284), processor 90 may continue to monitor heart 12 for tachyarrhythmias (280). If processor 90 has received a communication message from SICD 30 that a shock will be delivered or that a tachyarrhythmia has been detected ("YES" branch of block 284), processor 90 also enables shock detector 99 (286).

If shock detector 99 detects a delivered shock ("YES" branch of block 288), processor 90 may begin post-shock pacing to heart 12 of patient 14 (292). Processor 90 may start post-shock pacing by causing LPD 16 to enter a post-shock pacing mode. If no shock has been detected ("NO" branch of block 288), processor 90 may check to if the enabled shock detector period has timed out (290). Processor 90 may track a period of time since shock detector 99 was enabled, and if the period of time exceeds a timeout threshold ("YES" branch of block 290), processor 90 may disable shock detector 99 and continue to monitor ECGs for tachyarrhythmias (280). If the period after enabling shock detector 99 has not exceeded the timeout threshold ("NO" branch of block 290), processor 90 may continue to determine if any shocks have been detected (288).

In some examples, prior to delivering post-shock pacing, processor 90 may analyze sensed electrical signals from heart 12 to determine whether or not post-shock pacing is necessary. Processor 90 may analyze an ECG or other electrical signal to detect bradycardia and/or asystole. In response to the detection of bradycardia or asystole, processor 90 may begin post-shock pacing. Processor 90 may, in some example, determine one or more post-shock pacing parameters based on which rhythm was detected and/or characteristics of the detected rhythm. In response to not detecting bradycardia or asystole, processor 90 may withhold post-shock pacing and again look for any delivered shock (288).

After starting post-shock pacing (292), processor 90 may continue to determine if shock detector 99 detects any additional shocks from SICD 30 or another device (294). If processor 90 detects another shock ("YES" branch of block 294), processor 90 may restart the post-shock pacing (292). Processor 90 may also track a period of time following the delivery, or the starting of delivery, of post-shock pacing (296). If processor 90 determines that the period of time following initial delivery of post-shock pacing does not exceed a timeout threshold ("NO" branch of block 296), processor 90 will continue to determine if another shock has been detected (294). If, however, processor 90 determines that the period of time following starting of post-shock pacing exceeds the timeout threshold ("YES" branch of block 296), processor 90 may responsively terminate post-shock pacing (298). Processor 90 may then return to determine if another shock has been detected (288) or if the shock detector should be disabled (290). In other examples, processor 90 may continue post-shock pacing for an undetermined period of time following detection of the shock. In some examples, LPD 16 may even continue post-shock pacing during subsequent shocks.

In other examples, LPD 16 may not use a shock detector to time the beginning or ending of post-shock pacing. Instead, LPD 16 may determine when to deliver post-shock pacing based on a command from SICD 30. For example, SICD 30 may determine that a shock will be delivered and transmit a shock imminent command to LPD 16. In response to receiving the shock imminent command, LPD 16 may enter a shock state for a predetermined period of time. This predetermined period of time may be stored in memory 92 or sent along with the shock imminent command from SICD 30. The predetermined period of time may have a sufficient duration such that any shock would be delivered prior to the predetermined period expiring. In response to the predetermined period elapsing, LPD 16 may exit the shock state and enter a post-shock pacing state in which LPD 16 delivers post-shock pacing and/or first determines whether post-shock pacing is needed.

The systems and techniques described herein may be generally related to cooperative monitoring of a patient and/or therapy delivery to the patient using multiple implanted devices such as an SICD and an LPD. In one example, the SICD and LPD may detect the functions of each other and/or communicate to coordinate monitoring and therapy such as anti-tachyarrhythmia shock therapy and ATP. However, the SICD and LPD may coordinate other monitoring and therapy features. For example, using the communication techniques described herein, prior to either the SICD or LPD delivering therapy, sensed data from both devices may be used to determine if the therapy should be delivered. In some examples, the SICD or the LPD may be configured to override the other device in situations in which there is a discrepancy between whether or not physiological condition is occurring. In any case, the SICD and LPD may be configured to function together to monitor and/or provide therapy to patient 14.

The techniques described herein may provide for a SICD and LPD to operate cooperatively within a patient to monitor the heart for arrhythmias and deliver appropriate therapy to treat any detected arrhythmias. For example, an SICD and LPD may detect tachyarrhythmias and deliver anti-tachyarrhythmia shocks and/or anti-tachycardia pacing in an attempt to reestablish a sinus rhythm in the heart. Wireless communication between the SICD implanted external of the rib cage and one or more LPDs implanted within the heart may provide various ECG or EGM sensing vectors, shock capability, and ATP capability within traditional implantable pulse generators coupled to intravenous leads disposed in the heart.

The disclosure also contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to SICD 30, LPD 16, programmer 20, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between SICD 30, LPD 16 and/or programmer 20. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described for detecting arrhythmias and delivering anti-tachycardia therapy via a subcutaneous implantable cardioverter defibrillator and/or a leadless pacing device. Any combination of the described operations or functions is contemplated. These and other examples are within the scope of the following claims.

What is claimed is:

1. A method comprising:
   sensing a first electrical signal from a heart of a patient;
   detecting a tachyarrhythmia within the sensed first electrical signal;
   determining, by a subcutaneous implantable cardioverter defibrillator (SICD) and based on the detected tachyarrhythmia, to deliver anti-tachyarrhythmia shock therapy to the patient to treat the detected arrhythmia;
   receiving, by a leadless pacing device (LPD) implanted within the heart of the patient, communication from the SICD requesting the LPD deliver anti-tachycardia pacing to the heart;
   sensing, by the LPD, a second electrical signal from the heart of the patient; and
   determining, by the LPD and based on the second electrical signal, whether to deliver anti-tachycardia pacing to the heart from the LPD
   wherein determining whether to deliver anti-tachycardia pacing comprises determining, by the LPD and based on the second electrical signal, not to deliver anti-tachycardia pacing;
   wherein the method further comprises, in response to determining not to deliver anti-tachycardia pacing, transmitting, by the LPD and to the SICD, communication identifying the determination not to deliver anti-tachycardia pacing; and
   further comprising:
   receiving, by the SICD, the communication identifying the determination not to deliver anti-tachycardia pacing; and
   overturning, based on the received communication identifying the determination not to deliver anti-tachycardia pacing, the determination to deliver anti-tachyarrhythmia shock therapy to the patient.

2. A method comprising:
   sensing a first electrical signal from a heart of a patient;
   detecting a tachyarrhythmia within the sensed first electrical signal;
   determining, by a subcutaneous implantable cardioverter defibrillator (SICD) and based on the detected tachyarrhythmia, to deliver anti-tachyarrhythmia shock therapy to the patient to treat the detected arrhythmia;
   receiving, by a leadless pacing device (LPD) implanted within the heart of the patient, communication from the SICD requesting the LPD deliver anti-tachycardia pacing to the heart;

sensing, by the LPD, a second electrical signal from the heart of the patient; and
determining, by the LPD and based on the second electrical signal, whether to deliver anti-tachycardia pacing to the heart from the LPD
wherein determining whether to deliver anti-tachycardia pacing comprises determining, by the LPD and based on the second electrical signal, not to deliver anti-tachycardia pacing; and
further comprising:
determining, by the SICD, that the LPD did not deliver anti-tachycardia pacing; and
adjusting, by the SICD and based on the non-delivery of anti-tachycardia pacing, at least one of a tachyarrhythmia detection criteria and a therapy parameter.

3. A method comprising:
sensing a first electrical signal from a heart of a patient;
detecting a tachyarrhythmia within the sensed first electrical signal;
determining, by a subcutaneous implantable cardioverter defibrillator (SICD) and based on the detected tachyarrhythmia, to deliver anti-tachyarrhythmia shock therapy to the patient to treat the detected arrhythmia;
receiving, by a leadless pacing device (LPD) implanted within the heart of the patient, communication from the SICD requesting the LPD deliver anti-tachycardia pacing to the heart;
sensing, by the LPD, a second electrical signal from the heart of the patient; and
determining, by the LPD and based on the second electrical signal, whether to deliver anti-tachycardia pacing to the heart from the LPD;
in response to the determination to deliver anti-tachyarrhythmia shock therapy to the patient, transmitting, by the SICD and to the LPD, communication requesting the LPD deliver anti-tachycardia pacing to the heart and entering, by the SICD, an anti-tachycardia pacing detection mode for detecting anti-tachycardia pacing therapy delivered by the LPD; and
further comprising:
delivering, via one or more electrodes of the LPD, anti-tachycardia pacing to the heart of the patient;
detecting, by at least one electrode of the SICD, the delivered anti-tachycardia pacing therapy during the anti-tachycardia pacing detection mode;
transmitting, by the SICD and to the LPD, communication identifying that the delivered anti-tachycardia pacing has not captured a rhythm of the heart; and
determining, by the LPD, at least one updated parameter value that at least partially defines additional anti-tachycardia pacing.

4. A system comprising:
a subcutaneous implantable cardioverter defibrillator (SICD) comprising a first set of electrodes and configured to:
 sense a first electrical signal from a heart of a patient via the one or more first electrodes;
 detect a tachyarrhythmia within the sensed first electrical signal; and
 determine, based on the detected tachyarrhythmia, to deliver anti-tachyarrhythmia shock therapy to the patient to treat the detected arrhythmia; and
a leadless pacing device (LPD) comprising a second set of electrodes and configured to be implanted within the heart of the patient, wherein the LPD is configured to:
 receive communication from the SICD requesting the LPD deliver anti-tachycardia pacing to the heart;
 sense a second electrical signal from the heart of the patient via the second set of electrodes; and
 determine, based on the second electrical signal, whether to deliver anti-tachycardia pacing to the heart
wherein the LPD is configured to:
determine, based on the second electrical signal, not to deliver anti-tachycardia pacing, and
in response to the determination not to deliver anti-tachycardia pacing, transmit, to the SICD, communication identifying the determination not to deliver anti-tachycardia pacing; and
wherein the SICD is configured to:
receive the communication from the LPD identifying the determination not to deliver anti-tachycardia pacing; and
overturn, based on the received communication identifying the determination not to deliver anti-tachycardia pacing, the determination to deliver anti-tachyarrhythmia shock therapy to the patient.

5. A subcutaneous implantable cardioverter defibrillator (SICD), the SICD comprising:
a housing configured to be implanted in a patient external to a rib cage of the patient;
one or more electrodes configured to be disposed external to the rib cage;
a shock module configured to at least partially deliver anti-tachyarrhythmia shock therapy to a patient via the one or more electrodes;
a communication module configured to at least one of transmit or receive communication messages between a leadless pacing device (LPD) configured to be implanted within a heart of the patient;
a sensing module configured to sense an electrical signal from the heart of the patient via the one or more electrodes; and
a processor configured to:
 detect a tachyarrhythmia within the sensed electrical signal;
 determine, based on the detected tachyarrhythmia, to deliver anti-tachyarrhythmia shock therapy to the patient to treat the detected tachyarrhythmia; and
 transmit, via the communication module and prior to delivering anti-tachyarrhythmia shock therapy, a communication message to the LPD requesting the LPD deliver anti-tachycardia pacing to the heart of the patient.

6. A method comprising:
receiving, by a leadless pacing device (LPD), an indication of a detected cardiac arrhythmia eligible for anti-tachyarrhythmia shock therapy, wherein the LPD comprises a set of electrodes and is configured to be implanted within a heart of a patient;
in response to receiving the indication, enabling, by the LPD, a shock detector configured to detect delivery of anti-tachyarrhythmia shock therapy, wherein the LPD comprises the shock detector;
detecting, by the shock detector, delivery of anti-tachyarrhythmia shock therapy; and
in response to the detection, delivering, by the LPD and via at least a subset of the set of electrodes, post-shock pacing therapy to the heart of the patient; and
further comprising:
tracking, by the LPD, a period of time following detection of delivery of anti-tachyarrhythmia shock therapy;
determining, by the LPD, that the period of time exceeds a timeout threshold; and in response to the determination, disabling, by the LPD, the shock detector.

7. A method comprising:

receiving, by a leadless pacing device (LPD), an indication of a detected cardiac arrhythmia eligible for anti-tachyarrhythmia shock therapy, wherein the LPD comprises a set of electrodes and is configured to be implanted within a heart of a patient;

in response to receiving the indication, enabling, by the LPD, a shock detector configured to detect delivery of anti-tachyarrhythmia shock therapy, wherein the LPD comprises the shock detector;

detecting, by the shock detector, delivery of anti-tachyarrhythmia shock therapy; and in response to the detection, delivering, by the LPD and via at least a subset of the set of electrodes, post-shock pacing therapy to the heart of the patient; and wherein detecting delivery of anti-tachyarrhythmia shock therapy comprises detecting a first delivery of anti-tachyarrhythmia shock therapy, and wherein the method further comprises:

detecting a second delivery of anti-tachyarrhythmia shock therapy; and in response to the detection of the second delivery of anti-tachyarrhythmia shock therapy, re-starting, by the LPD, delivery of post-shock pacing therapy to the heart of the patient.

8. A method comprising:

receiving, by a leadless pacing device (LPD), an indication of a detected cardiac arrhythmia eligible for anti-tachyarrhythmia shock therapy, wherein the LPD comprises a set of electrodes and is configured to be implanted within a heart of a patient;

in response to receiving the indication, enabling, by the LPD, a shock detector configured to detect delivery of anti-tachyarrhythmia shock therapy, wherein the LPD comprises the shock detector;

detecting, by the shock detector, delivery of anti-tachyarrhythmia shock therapy; and in response to the detection, delivering, by the LPD and via at least a subset of the set of electrodes, post-shock pacing therapy to the heart of the patient; and further comprising:

tracking, by the LPD, a period of time following delivery of post-shock pacing therapy;

determining, by the LPD, that the period of time exceeds a timeout threshold; and in response to the determination, terminating, by the LPD, delivery of post-shock pacing therapy.

9. A subcutaneous implantable cardioverter defibrillator (SICD), the SICD comprising:

a housing configured to be implanted in a patient external to a rib cage of the patient;

one or more electrodes configured to be disposed external to the patient's heart;

a shock module configured to at least partially deliver anti-tachyarrhythmia shock therapy to a patient via the one or more electrodes;

a communication module configured to at least one of transmit or receive communication messages between a leadless pacing device (LPD) configured to be implanted within a heart of the patient;

a sensing module configured to sense an electrical signal from the heart of the patient via the one or more electrodes; and a processor configured to:

detect a tachyarrhythmia within the sensed electrical signal;

determine, based on the detected tachyarrhythmia, to deliver anti-tachyarrhythmia shock therapy to the patient to treat the detected tachyarrhythmia; and transmit, via the communication module and prior to delivering anti-tachyarrhythmia shock therapy, a communication message to the LPD requesting the LPD deliver anti-tachycardia pacing to the heart of the patient.

\* \* \* \* \*